(12) United States Patent
Warner et al.

(10) Patent No.: US 9,157,875 B2
(45) Date of Patent: *Oct. 13, 2015

(54) DRUG DEVELOPMENT AND MANUFACTURING

(76) Inventors: Benjamin P. Warner, Los Alamos, NM (US); T. Mark McCleskey, Los Alamos, NM (US); Anthony K. Burrell, Los Alamos, NM (US)

(*) Notice: Subject to any disclaimer, the term of this patent is extended or adjusted under 35 U.S.C. 154(b) by 697 days.

This patent is subject to a terminal disclaimer.

(21) Appl. No.: 10/880,388

(22) Filed: Jun. 29, 2004

(65) Prior Publication Data

US 2004/0235059 A1 Nov. 25, 2004

Related U.S. Application Data

(63) Continuation-in-part of application No. 09/859,701, filed on May 16, 2001, now Pat. No. 7,858,385, and a continuation-in-part of application No. 10/206,524, filed on Jul. 25, 2002, now abandoned, and a continuation-in-part of application No. 10/621,825, filed on Jul. 16, 2003, now Pat. No. 6,858,148.

(60) Provisional application No. 60/511,434, filed on Oct. 14, 2003, provisional application No. 60/513,086, filed on Oct. 21, 2003.

(51) Int. Cl.
*G01N 23/223* (2006.01)
*G01N 33/50* (2006.01)
*G01N 33/58* (2006.01)
*G01N 33/543* (2006.01)

(52) U.S. Cl.
CPC .............. *G01N 23/223* (2013.01); *G01N 33/50* (2013.01); *G01N 33/54373* (2013.01); *G01N 33/582* (2013.01); *G01N 2223/076* (2013.01); *G01N 2333/705* (2013.01); *Y10S 430/167* (2013.01); *Y10T 436/153333* (2015.01); *Y10T 436/156666* (2015.01); *Y10T 436/16* (2015.01); *Y10T 436/18* (2015.01)

(58) Field of Classification Search
None
See application file for complete search history.

(56) References Cited

U.S. PATENT DOCUMENTS

| | | | | |
|---|---|---|---|---|
| 4,436,826 A | * | 3/1984 | Wang | 436/525 |
| 4,528,267 A | * | 7/1985 | Calenoff et al. | 435/7.92 |
| 4,577,337 A | * | 3/1986 | Light | 378/44 |
| 4,663,277 A | * | 5/1987 | Wang | 435/5 |
| 5,143,854 A | | 9/1992 | Pirrung et al. | |
| 5,216,126 A | * | 6/1993 | Cox et al. | 530/350 |
| 5,667,764 A | * | 9/1997 | Kopia et al. | 424/1.45 |
| 5,902,723 A | | 5/1999 | Dower et al. | |
| 6,147,344 A | | 11/2000 | Annis et al. | |
| 6,329,209 B1 | | 12/2001 | Wagner et al. | |
| 6,344,334 B1 | | 2/2002 | Ellman et al. | |
| 6,391,590 B1 | * | 5/2002 | Sano et al. | 435/69.7 |
| 6,395,169 B1 | | 5/2002 | Hingsgaul et al. | |
| 6,432,696 B2 | * | 8/2002 | Custance et al. | 435/287.2 |
| 6,719,147 B2 | | 4/2004 | Strano et al. | |
| 7,101,677 B1 | * | 9/2006 | Milligan et al. | 435/7.2 |
| 7,858,385 B2 | * | 12/2010 | Warner et al. | 436/172 |
| 2003/0023562 A1 | | 1/2003 | Bailey et al. | |
| 2003/0027129 A1 | | 2/2003 | Warner et al. | |
| 2004/0004183 A1 | | 1/2004 | Bakajin et al. | |
| 2004/0017884 A1 | | 1/2004 | Havrilla et al. | |
| 2004/0093526 A1 | | 5/2004 | Hirsch | |
| 2004/0128518 A1 | | 7/2004 | Cavers et al. | |
| 2004/0235059 A1 | | 11/2004 | Burrell et al. | |
| 2005/0011818 A1 | | 1/2005 | Warner et al. | |
| 2005/0015596 A1 | | 1/2005 | Bowers | |
| 2005/0214847 A1 | | 9/2005 | Havrilla et al. | |

FOREIGN PATENT DOCUMENTS

| | | |
|---|---|---|
| JP | 2001-289802 | 10/2001 |
| JP | 2004028583 | 1/2004 |
| JP | 5143841 B2 | 2/2013 |

OTHER PUBLICATIONS

Goldin et al. "Quantitation of Antibody Binding to Cell Surface Antigens by X-ray Fluorescence Spectrometry" Biochimica et Biophysica Acta, 552 (1979) 120-128.*
Creighton, T. et al. "Proteins: Structures and Molecular Properties" (1993) 2nd Ed, W.H. Freeman and Company, New York, NY, pp. 5-6 and 348-350.*
Havrilla et al. ("Elemental screening of combinatorial chemical libraries using micro X-ray fluorescence" Abstracts of Papers, 221st ACS National Meeting, San Diego, CA, United States, Apr. 1-5, 2001).*
Curnis et al. "Differential Binding of Drugs Containing the NGR Motif to CD13 Isoforms in Tumor Vessels, Epithelia, and Myeloid Cells" Cancer Research 62, 867-874, Feb. 1, 2002.*
Beveridge et al. "Binding of an Inert, Cationic Osmium Probe to Walls of Bacillus subtilis". Journal of Bacteriology 149 (1982) 1120-1123.*
Miller et al. J. Comb. Chem. vol. 5 (2003), 245-252, published on the web Feb. 28, 203.*
Academic Press Dictionary of Science and Technology, definition for the term "chemical" (1992), Retrieved from http://www.credoreference.com/entry/apdst/chemical.*
Banks et al. "Impact of a Red-Shifted Dye Label for High Throughput Fluorescence Polarization Assays of G Protein-Coupled Receptors", Journal of Biomolecular Screening, vol. 5, No. 5 (2000), 329-334.*

(Continued)

*Primary Examiner* — Christine Foster
(74) *Attorney, Agent, or Firm* — Francesco de Rege Thesauro

(57) ABSTRACT

X-ray fluorescence (XRF) spectrometry has been used for detecting binding events and measuring binding selectivities between chemicals and receptors. XRF may also be used for estimating the therapeutic index of a chemical, for estimating the binding selectivity of a chemical versus chemical analogs, for measuring post-translational modifications of proteins, and for drug manufacturing.

5 Claims, No Drawings

(56) References Cited

OTHER PUBLICATIONS

Ruiz et al. "Quantification of Pt bound to DNA using total-reflection X-ray fluorescence (TXRF)" Analyst, 1999, 124, 583-585.*

DrugBank, "Cisplatin", Accession No. DB00515, retrieved from http://www.drugbank.ca/drugs/DB00515 on Aug. 8, 2013, three pages.*

The International Atomic Energy Agency, "Industrial and Environmental Applications of Nuclear Analytical Techniques", Nov. 1999, pp. 1-13 and 29-38, retrieved from http://www-pub.iaea.org/MTCD/publications/PDF/te_1121_prn.pdf.*

Heng Zhu and Michael Snyder, "Protein Chip Technology (Review)," *Current Opinion in Chemical Biology*, vol. 7, pp. 55-63, (2003).

Gavin MacBeath and Stuart L. Schreiber, "Printing Proteins as Microarrays for High-Throughput Function Determination," *Science*, vol. 289, pp. 1760-1763, (2000).

Eric T. Fung et al., "Protein Biochips for Differential Profiling,"*Analytical Biotechnology*, vol. 12, pp. 65-69, (2001).

Thomas Kukar et al., "Protein Microarrays to Detect Protein-Protein Interactions Using Red and Green Fluorescent Proteins," *Analytical Biochemistry*, vol. 306, pp. 50-54, (2002).

Grace Y.J. Chen et al., "Developing a Strategy for Activity-Based Detection of Enzymes in a Protein Microarray," *ChemBioChem*, pp. 336-339, (2003).

Karen Martin et al., "Quantitative Analysis of Protein Phosphorylation Status and Protein Kinase Activity on Microarrays Using a Novel Fluorescent Phosphorylation Sensor Dye," *Proteomics*, vol. 3, pp. 1244-1255, (2003).

Jonathan Burbaum, Gabriela M. Tobal, "Proteomics in Drug Discovery," *Current Opinion in Chemical Biology*, vol. 6, pp. 427-433, (2002).

Ilkka A. Hemmilä and Pertti Hurskainen, "Novel Detection Strategies for Drug Discovery," *Drug Discovery Today*, vol. 7, pp. S150-S156, pp. S150-S156, (2002).

Roger Ulrich and Stephen H. Friend, "Toxicogenomics and Drug Discovery: Will New Technologies Help Us Produce Better Drugs?," *Nature Reviews Drug Discovery*, vol. 1, pp. 84-88 (2002).

Jacob Sherman, "The Theoretical Derivation of Fluorescent X-Ray Intensities From Mixtures" *Spectrochimica Acta*, vol. 7, pp. 283-306 (1955).

Gordon M. Barrow, "Rates and Mechanisms of Chemical Reactions," Physical Chemistry, $5^{th}$ Ed., McGraw-Hill, NY, pp. 710-712, pp. 756-757, chapter 7, chapter 18 (1988).

Roger Perkins et al., "Quantitative Structure-Activity Relationship Methods: Perspectives on Drug Discovery and Toxicology," *Environmental Toxicology and Chemistry*, vol. 22, pp. 1666-1679 (2003).

T. Wayne Schultz et al., "Quantitative Structure-Activity Relationships (QSARs) in Toxicology: a Historical Perspective" *THEOCHEM*, vol. 622, pp. 1-22 (2003).

"Olanzapine (Zyprexa®)," Clinical Toxicology Review, vol. 18, No. 2, Mar. 1997.

Christopher A. Lipinski et al., "Experimental and Computational Approaches to Estimate Solubility and Permeability in Drug Discovery and Development Settings," *Advanced Drug Delivery Reviews*, vol. 23, pp. 3-25, (1997).

"Personalized Prescribing," Jean Wallace, The Scientist, 15[12]:10, Jun. 11, 2001.

English translation of Japanese Office Action for related Japanese Application No. 2009-532446, dated Jan. 31, 2012 (2 pages).

English translation of Japanese Office Action for related Japanese Application No. 2012-122988, dated Dec. 17, 2013 (3 pages).

English translation of Japanese Office Action for related Japanese Application No. 2012-122988, dated Apr. 23, 2013 (8 pages).

English translation of Japanese Office Action for related Japanese Application No. 2009-532446, dated Aug. 7, 2012 (2 pages).

Lankosz et al., Spectrochemica Acta Part B vol. 59 (2004) pp. 1517-1521 (5 pages) Sep. 13, 2004.

Rindby et al., J. Synchroton Radiation, Jul. 1, 1997, vol. 4, No. 4, pp. 228-235 Abstract only (1 page).

Nagata et al., X-Ray Spectrometry Epub Oct. 24, 2005, vol. 35, No. 1, pp. 79-84 Abstract only (4 pages).

Supplemental European Search Report for EP07874491, mailed Jan. 26, 2010 (6 pages).

European Search Report Written Opinion for EP07874491, mailed Jan. 26, 2010 (6 pages).

International Preliminary Report on Patentability for PCT/US07/21888, dated May 30, 2010 (13 pages).

Communication from Examining Division regarding EP07874491, mailed Nov. 26, 2010 (6 pages).

Communication from Examining Division regarding EP07874491, mailed Jun. 24, 2011 (4 pages).

Communication from Examining Division regarding Intention to Grant EP07874491, mailed Mar. 5, 2012 (4 pages).

Potts et al., J. Analyt. Atomic Spectrom., Issue 10, 2006 Abstract only (2 pages).

Eurpean Search Report for EP12164870 (2 pages), Dated Jan. 25, 2013.

European Search Report Opinion for EP12164870 (4 pages), Dated Jan. 25, 2013.

Communication from Examining Division regarding EP12164870, Dated May 11, 2013 (4 pages).

Communication from Examining Division regarding EP12164870, Dated Apr. 15, 2014 (4 pages).

Goldin et al., Biochem e Biophys Acta, 552 (1979) 120-128 Abstact only (2 pages).

Miller et al., J. Comb. Chem., vol. 5 (2003) pp. 245-252 epub Feb. 28, 2003, Abstract only (2 pages).

Zhu et al., Current Opinion in Chemical Biology, vol. 7, pp. 55-63, (2003). (9 pages).

MacBeath et al., Schreiber, Science, vol. 289, pp. 1760-1763, (2000) (4 pages).

Fung et al., "Protein Biochips for Differential Profiling," Analytical Biotechnology, vol. 12, pp. 65-69, (2001) (5 pages).

Kukar et al., Analytical Biochemistry, vol. 306, pp. 50-54, (2002) (5 pages).

Chen et al., ChemBioChem, pp. 336-339, (2003) (4 pages).

Martin et al., Proteomics, vol. 3, pp. 1244-1255, (2003) (12 pages).

Burbaum etal., Current Opinion in Chemical Biology, vol. 6, pp. 427-433, (2002) (7 pages).

Hemmila et al., Drug Discovery Today, vol. 7, pp. S150-S156, pp. S150-S156, (2002) (7 pages).

Ulrich e al., Nature Reviews Drug Discovery, vol. 1, pp. 84-88 (2002) (6 pages).

Sherman, Spectrochimica Acta, incorporated by reference herein, vol. 7, pp. 283-306 (1955) (24 pages).

Barrow, "Rates and Mechanisms of Chemical Reactions," Physical Chemistry, 5th Ed., McGraw-Hill, NY, pp. 710-712, pp. 756-757, chapter7, chapter 18 (1988) (94 pages).

Ricci et al., X-Ray Spectrometry, Heyden & Sons Ltd., epub Apr. 11, 2005 Abstract only (3 pages).

Mertens et al. Spectra Acta Part BL Atomic Spectroscopy, vol. 56, Isue 11, Nov. 30, 2001, pp. 2157-2164, Abstract only (2 pages).

International Search Report for PCT/US07/21888, mailed Mar. 5, 2009, (4 pages).

Machine translation of claims for Japanese patent application No. 2000-113225, filed Apr. 10, 2000 (1 page).

Machine translation of Detailed Description for Japanese patent application No. 2000-113225, filed Apr. 10, 2000 (13 pages).

Machine translation for Claims for Japanese Patent No. 5143841 (48 pages).

Machine translation for Detailed Description for Japanese Patent No. 5143841 (129 pages).

Machine translation for Claims for Japanese patent publication 2004028583 (2 pages).

Machine translation for Detailed Description for Japanese patent publication 2004028583 (8 pages).

* cited by examiner

DRUG DEVELOPMENT AND MANUFACTURING

CROSS-REFERENCE TO RELATED APPLICATIONS

This application is a continuation-in-part of U.S. patent application Ser. No. 09/859,701, now U.S. Pat. No. 7,858,385, now U.S. Patent Application 20030027129 entitled "Method for Detecting Binding Events Using Micro-X-ray Fluorescence Spectrometry," which was published on Feb. 6, 2003, and a continuation-in-part of U.S. patent application Ser. No. 10/206,524, now abandoned, and a continuation-in-part of U.S. patent application Ser. No. 10/621,825 filed Jul. 16, 2003, now U.S. Pat. No. 6,858,148, and claims the benefit of U.S. Provisional Application Ser. No. 60/511,434 filed Oct. 14, 2003, and claims the benefit of U.S. Provisional Application Ser. No. 60/513,086 filed Oct. 21, 2003, all hereby incorporated by reference herein.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to detecting binding events and more particularly to estimating binding selectivities for chemicals, analogs, and drugs being tested with receptors and then manufacturing those having a high binding selectivity to the receptors.

BACKGROUND OF THE INVENTION

The desire to hasten the identification of potentially important drugs, catalysts, chemical and biological sensors, medical diagnostics, and other materials is a constant challenge that has prompted the use of combinatorial synthetic and screening strategies for synthesizing these materials and screening them for desirable properties. Combinatorial synthesis involves assembling a "library", i.e. a very large number of chemically related compounds and mixtures, usually in the form of an array on a substrate surface. High throughput screening of an array involves identifying which members of the array, if any, have the desirable property or properties. The array form facilitates the identification of a particular material on the substrate. Combinatorial arrays and high-throughput screening techniques have been used to solve a variety of problems related to the development of biological materials such as proteins and DNA because the screening techniques can be used to rapidly assay many biological materials.

The binding properties of a protein largely depend on the exposed surface amino acid residues of its polypeptide chain (see, for example, Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000). These amino acid residues can form weak noncovalent bonds with ions and molecules. Effective binding generally requires the formation of many weak bonds at a "binding site," which is usually a cavity in the protein formed by a specific arrangement of amino acids. There should be a precise fit with the binding site for effective binding to occur.

The chemical properties and in particular, the binding properties of a protein depend almost entirely on the exposed surface amino acid residues of the polypeptide chain. These residues can form weak noncovalent bonds with other molecules. An effective binding between the protein, one example of a group of materials herein referred to as "receptors", and the material that binds to the receptor, referred to herein as "chemical", generally requires that many weak bonds form between the protein receptor and the chemical. Chemicals include organic molecules, inorganic molecules, salts, metal ions, and the like. The bonds between the protein and the chemical form at the "binding site" of the protein. The binding site is usually a cavity in the protein that is formed by a specific arrangement of amino acids that often belong to widely separated regions of the polypeptide chain and represent only a minor fraction of the total number of amino acids present in the chain. Chemicals should fit precisely into the binding site for effective binding to occur. The shape of these binding sites can differ greatly among different proteins, and even among different conformations of the same protein. Even slightly different conformations of the same protein may differ greatly in their binding abilities. For further discussion of the structure and function of proteins, see: Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000.

After a receptor array is prepared, it is screened to determine which members have the desirable property or properties. U.S. Pat. No. 5,143,854 to M. C. Pirrung et al. entitled "Large Scale Photolithographic Solid Phase Synthesis of Polypeptides and Receptor Binding Screening Thereof", which issued Sep. 1, 1992, hereby incorporated by reference, describes one such screening method. A polypeptide array is exposed to a ligand (an example of a chemical) to determine which members of the array bind to the ligand. The ligands described are radioactive, or are "tagged", i.e. attached via one or more chemical bonds to a chemical portion that fluoresces when exposed to non-ionizing, ultraviolet radiation. Thus, the attached portion, i.e. the tag, makes the chemical visible by interrogation with ultraviolet radiation. Tagged molecules have also been used to aid in sequencing immobilized polypeptides as described, for example, in U.S. Pat. No. 5,902,723 to W. J. Dower et al. entitled "Analysis of Surface Immobilized Polymers Utilizing Microfluorescence Detection," which issued May 11, 1999. Immobilized polypeptides are exposed to molecules labeled with fluorescent tags. The tagged molecules bind to the terminal monomer of a polypeptide, which is then cleaved and its identity determined. The process is repeated to determine the complete sequence of the polypeptide.

It is generally assumed that the attachment of a fluorescent tag to a chemical only serves to make visible the otherwise invisible chemical, and does not alter its binding properties. Since it is well known that even small changes to the structure of a molecule could affect its function, this assumption that a tagged chemical, i.e. a "surrogate", has the same binding affinity as the untagged chemical may not be a valid one. Small structural changes that accompany even a conformational change of a receptor have been known to affect the binding affinity of the receptor. The tagged surrogates are structurally different from their untagged counterparts, and these structural differences could affect their binding affinities. Since binding affinities derived using tagged surrogates are suspect, the binding properties of receptors and chemicals should be evaluated using the untagged chemical or receptor and not with a tagged surrogate.

Pharmaceutical chemicals are the active ingredients in drugs, and it is believed that their therapeutic properties are linked to their ability to bind to one or more binding sites. The shapes of these binding sites may differ greatly among different proteins, and even among different conformations of the same protein. Even slightly different conformations of the same protein may differ greatly in their binding abilities. For these reasons, it is extremely difficult to predict which chemicals will bind effectively to proteins.

Development and manufacturing for a new pharmaceutical chemical for a drug, i.e. drug development, generally involves determining the binding affinities between a potential pharmaceutical chemical (preferably a water soluble organic chemical that can dissolve into the blood stream) and a receptor (generally a biological material such as an enzyme or non-enzyme protein, DNA, RNA, human cell, plant cell, animal cell, and the like) at many stages of the drug development process. The receptor may also be a microorganism (e.g. prion, virus, bacterium, spores, and the like) in whole or in part. The drug development process typically involves procedures for combining potential pharmaceutical chemicals with receptors, detecting chemical binding between the potential pharmaceutical chemicals and the receptors and determining the binding affinity and kinetics of binding of a receptor to a chemical to form a complex or the kinetics of release of a bound chemical from a complex. The binding affinity is defined herein as the associative equilibrium constant Ka for the following equilibrium expression:

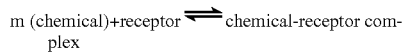

The binding affinity, Ka, is defined by equation (1) below.

$$Ka = [\text{chemical-receptor complex}]/[\text{receptor}][\text{chemical}]^m \quad (1)$$

In equation (1), [chemical-receptor complex] is the concentration in moles per liter of the chemical-receptor complex, [receptor] is the concentration in moles per liter of the receptor, 'm' is the number of molecules of chemical that bind to each molecule of receptor, and [chemical] is the concentration in moles per liter of the chemical. Any effects due to concentration can be simplified if the concentration of chemical used were the same for all receptors.

Nowadays, the drug development process may involve the rapid screening of hundreds or thousands of chemicals in order to identify a "lead compound," which is one of the many tested that binds very strongly, i.e. has a high binding affinity, with a particular receptor. After such a lead compound has been identified, then other potential pharmaceutical chemicals similar in structure to the lead compound, which are referred to herein as "analogs" of the lead compound, are synthesized and tested in order to determine which of these chemicals, if any, exhibits an even higher binding affinity.

The preparation and high-throughput screening of biological arrays is exemplified by the following papers: H. Zhu and M. Snyder, "Protein Chip Technology (Review)," *Current Opinion in Chemical Biology*, vol. 7, pp. 55-63, (2003); G. MacBeath and S. L. Schreiber, "Printing Proteins As Microarrays For High-Throughput Function Determination," *Science*, vol. 289, pp. 1760-1763, (2000); E. T. Fung et al., "Protein biochips for differential profiling," *Analytical Biotechnology*, Vol. 12, pp. 65-69, (2001); T. Kukar et al., "Protein Microarrays to Detect Protein-Protein Interactions Using Red and Green Fluorescent Proteins," *Analytical Biochemistry*, vol. 306, pp. 50-54, (2002); G. Y. J. Chen et al., "Developing a Strategy for Activity-Based Detection of Enzymes in a Protein Microarray," *ChemBioChem*, pp. 336-339, (2003); K. Martin et al., "Quantitative analysis of protein phosphorylation status and protein kinase activity on microarrays using a novel fluorescent phosphorylation sensor dye," *Proteomics*, Vol. 3, pp. 1244-1255, (2003); J. Burbaum and G. M. Tobal, "Proteomics in drug discovery," *Current Opinion in Chemical Biology*, Vol. 6, pp. 427433, (2002); I. A. Hemmilä and P. Hurskainen, "Novel detection strategies for drug discovery," *Drug Discovery Today*, Vol. 7, pp. $S^{150}$-$S^{156}$, (2002), Pages S150-S156; all incorporated herein by reference.

Some screening methods are described in the following patents, all of which are hereby incorporated by reference.

U.S. Pat. No. 6,147,344 to D. Allen Annis et al. entitled "Method for Identifying Compounds in a Chemical Mixture", which issued Nov. 14, 2000, describes a method for automatically analyzing mass spectrographic data from mixtures of chemical compounds.

U.S. Pat. No. 6,344,334 to Jonathan A. Ellman et al. entitled "Pharmacophore Recombination for the Identification of Small Molecule Drug Lead Compounds," which issued Feb. 5, 2002, describes a method for identifying a drug lead compound by contacting target biological molecules with cross-linked binding fragments.

U.S. Pat. No. 6,395,169 to Ole Hindsgaul et al. entitled "Apparatus for Screening Compound Libraries," which issued May 28, 2002, describes an apparatus that employs frontal chromatography combined with mass spectrometry to identify and rank members of a library that bind to a target receptor.

Other current high-throughput screening methods, along with their associated drawbacks, are listed in TABLE 1 below, which is taken from the following paper: H. Zhu and M. Snyder, "Protein Chip Technology (Review)," *Current Opinion in Chemical Biology*, vol. 7, pp. 55-63, (2003).

TABLE 1

| Detection Technique | Probe Labeling | Data Acquisition |
| --- | --- | --- |
| ELISA (Enzyme-Linked Immunosorbent Assay) | Enzyme-Linked Antibodies | CCD Imaging |
| Isotopic Labeling | Radioisotope Labeled Analyte | X-Ray Film Or Phospoimager |
| Sandwich Immunoassay | Fluorescently Labeled Antibodies | Laser Scanning |
| Surface Plasmon Resonance | Receptor must be attached to a surface | Refractive Index Change |
| Non-Contact Atomic Force Microscopy | None | Surface Topological Change |
| Planar Waveguide | Fluorescently Labeled Antibodies | CCD Imaging |

TABLE 1-continued

| Detection Technique | Probe Labeling | Data Acquirement |
| --- | --- | --- |
| SELDI (Surface Enhanced Laser Desorption Ionization Mass Spectrometry) | None | Mass Spectrometry |
| Electrochemical | Metal-Coupled Analyte | Conductivity Measurement |

TABLE 1 shows that most of the listed screening methods have the same drawback: they require either radiolabeled chemicals, chemicals that have been altered with a fluorescent tag, or chemicals that have been altered with a metal tag.

X-ray fluorescence (XRF) spectrometry is a powerful spectroscopic technique that has been used to determine the elements that are present in a chemical sample, and to determine the quantity of those elements in the sample. The underlying physical principle of the method is that when an atom of a particular element is irradiated with X-ray radiation, the atom ejects a core electron such as a K shell electron. The resulting atom is in then an excited state, and it can return to the ground state by replacing the ejected electron with an electron from a higher energy orbital. This is accompanied by the emission of a photon, i.e. X-ray fluorescence, and the photon energy is equal to the difference in the energies of the two electrons. Each element has a characteristic set of orbital energies and therefore, a characteristic X-ray fluorescence (XRF) spectrum.

An XRF spectrometer is an apparatus capable of irradiating a sample with an X-ray beam, detecting the X-ray fluorescence from an element included in the sample, and using the X-ray fluorescence to determine which elements are present in the sample and providing the quantity of these elements. A typical, commercially available X-ray fluorescence spectrometer is the EDAX Eagle XPL energy dispersive X-ray fluorescence spectrometer, equipped with a microfocus X-ray tube, lithium drifted silicon solid-state detector, processing electronics, and vendor supplied operating software. In principle, any element may be detected and quantified with XRF.

U.S. patent application 20030027129 entitled "Method for Detecting Binding Events Using Micro-X-ray Fluorescence Spectrometry," incorporated by reference herein, describes a method for detecting binding events using micro-x-ray fluorescence spectrometry. According to the '129 patent application, receptors are exposed to at least one potential chemical and arrayed on a substrate support. Each member of the array is exposed to X-ray radiation. The magnitude of a detectable x-ray fluorescence signal for at least one element can be used to determine whether a binding event between a chemical and a receptor has occurred, and can provide information related to the extent of binding between the chemical and receptor.

U.S. patent application 20040017884 entitled "Flow Method And Apparatus For Screening Chemicals Using Micro X-Ray Fluorescence," which was published on Jan. 29, 2004, incorporated by reference herein, describes a method for identifying binding events between potential pharmaceutical chemicals and receptors (e.g. proteins). The method involves modifying a mixture of potential pharmaceutical chemicals by adding at least one receptor to the mixture. After allowing sufficient time for any bound complex between any of the potential pharmaceutical chemicals and any of the receptors to form, if such a complex can form, the resulting solution is flow separated into at least two components. Each component is exposed to an x-ray excitation beam. If the exposed component emits a detectable x-ray fluorescence signal, that component is isolated. The identity of any isolated component can be determined using one or more standard analytical techniques, such as gas chromatography, liquid chromatography, mass spectrometry, nuclear magnetic resonance spectroscopy, infrared spectroscopy, ultraviolet spectroscopy, visible spectroscopy, elemental analysis, cell culturing, immunoassaying, and the like.

Effective drugs are selective drugs; they bind to a specific desired receptor, bypassing other receptors, to produce a desired therapeutic effect. This way, they target a specific disease in the body with minimal side effects; selectivity provides efficacy without undesirable side effects.

The therapeutic index is a measure of drug selectivity that is ordinarily calculated from data obtained from experiments with animals. The therapeutic index of the drug is typically defined as the ratio of two numbers, LD50/ED50, where LD50 is the dose of a drug that is found to be lethal (i.e. toxic) for 50 percent of the population of animals used for testing the drug, and ED50 is the dose of the drug that is found to have a therapeutic effect for 50 percent of that population. More broadly, it is a measure of the how much of the drug is needed to produce a harmful effect relative to the amount needed to produce a beneficial effect. The ratio LD50/ED50 is therefore, a measure of the approximate "safety factor" for a drug; a drug with a high therapeutic index can presumably be administered with greater safety than one with a low index.

Estimating the therapeutic index of a chemical involves measuring the binding affinity of a chemical to a first receptor, and measuring the binding affinity of the same chemical to a second receptor. After measuring these binding affinities, the ratio of the binding affinity of the chemical divided by the amount of first receptor versus the binding affinity of the chemical divided by the amount of the second receptor is determined. This ratio is provides an estimate of the "therapeutic index". For an example of using DNA arrays with optical fluorescence high-throughput screening to estimate a therapeutic index, see for example, R. Ulrich and S. H. Friend, "Toxicogenomics and Drug Discovery: Will New Technologies Help Us Produce Better Drugs?," *Nature Reviews Drug Discovery*, v.1, pp.84-88 (2002), incorporated herein by reference.

There remains a need for simpler methods for measuring binding affinities and selectivities, estimating the therapeutic index of a chemical, and for expediting drug manufacturing, Therefore, an object of the present invention is to provide a method for measuring binding affinities of chemicals.

Another object of the present invention is to provide a method for measuring selectivity of chemicals binding to receptors.

Yet another object of the invention is to provide a method for estimating the therapeutic index of a chemical.

Still another object of the invention is to provide a method that employs x-ray fluorescence for drug manufacture.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a method for estimating the binding selectivity of a chemical having at least one heavy element (i.e. an element having an atomic number of nine or higher) to at least two receptors. The method includes establishing a baseline X-ray fluorescence signal for a heavy element in a portion of a first receptor and in a portion of at least one more receptor that may be the same or different from the first receptor, the heavy element being present in a chemical to be tested for binding to the receptors; exposing the receptors to the chemical and allowing the chemical to bind to them to form a first chemical-receptor complex and at least one more chemical-receptor complex; measuring the x-ray fluorescence signals due to the heavy element in the first chemical-receptor complex and in the at least one more chemical-receptor complex; subtracting the baseline x-ray fluorescence signal of the first receptor from the measured x-ray fluorescence signal of the of the first chemical-receptor complex to obtain a first net x-ray fluorescence signal; subtracting the baseline x-ray fluorescence signal of the at least one more receptor from the measured x-ray fluorescence signal of the of the at least one more chemical-receptor complex to obtain at least one more net x-ray fluorescence signal; and then estimating the selectivity of the chemical by dividing the first net x-ray fluorescence signal by the amount of receptor in the portion of the first receptor to obtain a first quotient, dividing the at least one more net x-ray fluorescence signal by the amount of receptor in the portion of the at least one more receptor to obtain at least one more quotient, and then comparing the first quotient to the at least one more quotient.

The invention also includes a method for estimating the binding selectivity of a chemical versus at least one analog of the chemical to at least two receptors, the chemical and the at least one analog each having at least one heavy element. The method includes establishing a baseline x-ray fluorescence signal for a first heavy element in a first portion of a first receptor and in a first portion of a second receptor, the first heavy element being present in a chemical to be tested for binding to the receptors; establishing a baseline x-ray fluorescence signal for a second heavy element in a second portion of the first receptor and in a second portion of a second receptor, the second heavy element being present in an analog of the chemical to be tested for binding to the receptors; exposing the first portions of the receptors to the chemical and allowing the chemical to bind to them to form a first chemical-receptor complex and a second chemical-receptor complex; measuring the x-ray fluorescence signal due to the first heavy element present in the first chemical-receptor complex and in the second chemical-receptor complex; exposing the second portions of the receptors to the analog and allowing the analog to bind to them to form a first analog-receptor complex and a second analog-receptor complex; measuring the x-ray fluorescence signal due to the second heavy element present in the first analog-receptor complex and in the second analog-receptor complex; calculating the net x-ray fluorescence signal due to the first heavy element in the first chemical-receptor complex by subtracting the baseline x-ray fluorescence signal of the first portion of the first receptor from the measured x-ray fluorescence signal of the of the first chemical-receptor complex; calculating the net x-ray fluorescence signal due to the first heavy element present in the second chemical-receptor complex by subtracting the baseline x-ray fluorescence signal of the first portion of the second receptor from the measured x-ray fluorescence signal of the second chemical-receptor complex; calculating the net x-ray fluorescence signal due to the second heavy element in the first analog-receptor complex by subtracting the baseline x-ray fluorescence signal of the second portion of the first receptor from the measured x-ray fluorescence signal of the of the first analog-receptor complex; calculating the net x-ray fluorescence signal due to the second heavy element present in the second analog-receptor complex by subtracting the baseline x-ray fluorescence signal of the second portion of the second receptor from the measured x-ray fluorescence signal of the second analog-receptor complex; estimating the selectivity of the chemical to binding to the receptors by dividing the net x-ray fluorescence of the first chemical-receptor complex by the amount of receptor in the first portion of the first receptor to obtain a first quotient, dividing the net x-ray fluorescence of the second chemical-receptor complex by the amount of receptor in the first portion of the second receptor to obtain a second quotient; estimating the selectivity of the analog to binding to the receptors by dividing the net x-ray fluorescence of the first analog-receptor complex by the amount of receptor in the second portion of the first receptor to obtain a third quotient, dividing the net x-ray fluorescence of the second analog-receptor complex by the amount of receptor in the second portion of the second receptor to obtain a fourth quotient; and comparing first quotient to the second quotient to the third quotient to the fourth quotient.

The invention also includes a method for manufacturing a drug. The method includes establishing a baseline X-ray fluorescence signal for a heavy element in a portion of a first receptor and in a portion of at least one more receptor that may be the same or different from the first receptor, the heavy element being present in a chemical to be tested for binding to the receptors; exposing the receptors to the chemical and allowing the chemical to bind to them to form a first chemical-receptor complex and at least one more chemical-receptor complex; measuring the x-ray fluorescence signals due to the heavy element in the first chemical-receptor complex and in the at least one more chemical-receptor complex; subtracting the baseline x-ray fluorescence signal of the first receptor from the measured x-ray fluorescence signal of the of the first chemical-receptor complex to obtain a first net x-ray fluorescence signal; subtracting the baseline x-ray fluorescence signal of the at least one more receptor from the measured x-ray fluorescence signal of the of the at least one more chemical-receptor complex to obtain at least one more net x-ray fluorescence signal; estimating the selectivity of the chemical by dividing the first net x-ray fluorescence signal by the amount of receptor in the portion of the first receptor to obtain a first quotient, dividing the at least one more net x-ray fluorescence signal by the amount of receptor in the portion of the at least one more receptor to obtain at least one more quotient, and then comparing the first quotient to the at least one more quotient; and manufacturing the chemical in sufficient quantity for use as a drug if the first quotient and the at least one more quotient are different by at least one percent.

The invention also includes a method for manufacturing a drug. The method includes establishing a baseline X-ray fluorescence signal for a first heavy element in a first portion of a first receptor and in a first portion of a second receptor, the first heavy element being present in a chemical to be tested for binding to the receptors; establishing a baseline X-ray fluorescence signal for a second heavy element in a second portion of the first receptor and in a second portion of a second receptor, the second heavy element being present in an analog of the chemical to be tested for binding to the receptors; exposing the first portions of the receptors to the chemical and allowing the chemical to bind to them to form a first chemical-receptor complex and a second chemical-receptor complex; measuring the x-ray fluorescence signal due to the first heavy element present in the first chemical-receptor complex and in the second chemical-receptor complex; exposing the second portions of the receptors to the analog and allowing the analog to bind to them to form a first analog-receptor complex and a second analog-receptor complex; measuring the x-ray fluorescence signal due to the second heavy element present in the first analog-receptor complex and in the second analog-receptor complex; calculating the net x-ray fluorescence signal due to the first heavy element in the first chemical-receptor complex by subtracting the baseline x-ray fluorescence signal of the first portion of the first receptor from the measured x-ray fluorescence signal of the of the first chemical-receptor complex; calculating the net x-ray fluorescence signal due to the first heavy element present in the second chemical-receptor complex by subtracting the baseline x-ray fluorescence signal of the first portion of the second receptor from the measured x-ray fluorescence signal of the second chemical-receptor complex; calculating the net x-ray fluorescence signal due to the second heavy element in the first analog-receptor complex by subtracting the baseline x-ray fluorescence signal of the second portion of the first receptor from the measured x-ray fluorescence signal of the of the first analog-receptor complex; calculating the net x-ray fluorescence signal due to the second heavy element present in the second analog-receptor complex by subtracting the baseline x-ray fluorescence signal of the second portion of the second receptor from the measured x-ray fluorescence signal of the second analog-receptor complex; estimating the selectivity of the chemical to binding to the receptors by dividing the net x-ray fluorescence of the first chemical-receptor complex by the amount of receptor in the first portion of the first receptor to obtain a first quotient, dividing the net x-ray fluorescence of the second chemical-receptor complex by the amount of receptor in the first portion of the second receptor to obtain a second quotient; estimating the selectivity of the analog to binding to the receptors by dividing the net x-ray fluorescence of the first analog-receptor complex by the amount of receptor in the second portion of the first receptor to obtain a third quotient, dividing the net x-ray fluorescence of the second analog-receptor complex by the amount of receptor in the second portion of the second receptor to obtain a fourth quotient; and comparing first, second, third, and fourth quotients to determine if the chemical or analog is the more selective and manufacturing the more selective one in sufficient quantity for use as a drug.

The invention also includes a method for comparing the ability of at least one chemical in a first solution to bind to a portion of at least one receptor versus the ability of that chemical in a second solution to bind to a separate portion of the same at least one receptor. The method includes establishing a baseline X-ray fluorescence signal for a heavy element in a first portion of a receptor and for the heavy element in a separate portion of the receptor, the heavy element being present in a chemical that is being tested for binding to the receptor; exposing the first portion of the receptor to a first solution that includes the chemical, and allowing the chemical to bind to the receptor to form a first chemical-receptor complex; exposing the separate portion of the receptor to a second solution also includes the chemical, and allowing the chemical to bind to the receptor to form a second chemical-receptor complex; measuring the x-ray fluorescence signals due to the heavy element in the first chemical-receptor complex and in the second chemical-receptor complex; calculating the net x-ray fluorescence signal due to the heavy element in the first chemical-receptor complex by subtracting the baseline x-ray fluorescence signal of the first portion of receptor from the measured x-ray fluorescence signal of the first chemical-receptor complex; calculating the net x-ray fluorescence signal due to the heavy element in the second chemical-receptor complex by subtracting the baseline x-ray fluorescence signal of the separate portion of receptor from the measured x-ray fluorescence signal of the second chemical-receptor complex; and estimating the binding selectivity of the chemical in the first solution versus the second solution by dividing the net x-ray fluorescence signal of the first chemical-receptor complex by the amount of receptor in the first portion of the receptor to obtain a first quotient, dividing the net x-ray fluorescence of the second chemical-receptor complex by the amount of receptor in the separate portion of the receptor to obtain a second quotient, and then comparing the first quotient to the second quotient.

The invention also includes a method for estimating the relative effectiveness of at least two drugs, each drug having at least one heavy element. The method includes providing a sample from a medical patient, the sample comprising at least a first portion and a second portion of a first receptor and a first portion and a second portion of a second receptor; establishing a baseline X-ray fluorescence signal for a first heavy element in the first portion of the first receptor and in the first portion of the second receptor, the first heavy element being present in a first drug to be tested for binding to the first and second receptors; establishing a baseline X-ray fluorescence signal for a second heavy element in the second portion of the first receptor and in the second portion of the second receptor, the second heavy element being present in a second drug to be tested for binding to first and second receptors; exposing the first portion of the first receptor and the first portion of the second receptor to the first drug and allowing the drug to bind to the first receptor to form a first drug-receptor complex, and to bind to the second receptor to form a second drug-receptor complex; measuring the x-ray fluorescence signal due to the first heavy element present in the first drug-receptor complex and in the second drug-receptor complex; exposing the second portion of the first receptor and the second portion of the second receptor to the second drug and allowing the second drug to bind to the first receptor to form a third drug-receptor complex, and to bind to the second receptor to form a fourth drug-receptor complex; measuring the x-ray fluorescence signal due to the second heavy element present in the third drug-receptor complex and in the fourth drug-receptor complex; calculating a first net x-ray fluorescence signal due to the first heavy element present in the first drug-receptor complex by subtracting the baseline x-ray fluorescence signal of the first portion of the first receptor from the measured x-ray fluorescence signal of the of the first drug-receptor complex; calculating a second net x-ray fluorescence signal due to the first heavy element present in the second drug-receptor complex by subtracting the baseline x-ray fluorescence signal of the first portion of the second receptor from the measured x-ray fluorescence signal of the second drug-receptor complex; calculating a third net x-ray fluorescence signal due to the second heavy element in the third drug-receptor complex by subtracting the baseline x-ray fluorescence signal of the second portion of the first receptor from the measured x-ray fluorescence signal of the of the third drug-receptor complex; calculating a fourth net x-ray fluorescence signal due to the second heavy element present in the fourth drug-receptor complex by subtracting the baseline x-ray fluorescence signal of the second portion of the second receptor from the measured x-ray fluorescence signal of the fourth drug-receptors complex; calculating binding quotients for the first drug by dividing the first net x-ray fluorescence signal by the amount of receptor in the first portion of the first receptor to obtain a first quotient, dividing the second net x-ray fluorescence signal by the amount of receptor in the first portion of the second receptor to obtain a second quotient; calculating binding quotients for the second drug by dividing the third net x-ray fluorescence signal by the amount of receptor in the second portion of the first receptor to obtain a third quotient, dividing the fourth net x-ray fluorescence signal by the amount of receptor in the second portion of the second receptor to obtain a fourth quotient; and comparing the first, second, third, and fourth quotients to estimate the relative effectiveness of the first drug versus the second drug.

The invention also includes a method for estimating binding affinity. The method involves depositing a portion of a receptor on a substrate; establishing a baseline X-ray fluorescence signal for a heavy element in the portion of the receptor, the heavy element being present in a chemical being testing for binding to the receptor; exposing the receptor to a solution comprising the chemical at a first temperature, and allowing the chemical to bind to the receptor to form a chemical-receptor complex; measuring the x-ray fluorescence signal due to the heavy element in the chemical-receptor complex using excitation photons having an energy of at least 300 electron-volts to electronically excite the heavy element, and detecting emission photons using an x-ray detector having a dead time, the emission photons being generated from an excited state of the heavy element, the excited state of the heavy element having a fluorescence lifetime that is less than the dead time of the x-ray detector; calculating the net x-ray fluorescence signal due to the heavy element in the chemical-receptor complex by subtracting the baseline x-ray fluorescence signal of the portion of receptor from the measured x-ray fluorescence signal of the chemical-receptor complex; and estimating the binding affinity of the chemical for the receptor by dividing the net x-ray fluorescence signal of the chemical-receptor complex by the amount of the receptor in the portion of the receptor.

The invention also includes a method for detecting protein modification. The method includes establishing a baseline X-ray fluorescence signal for a heavy element in a portion of a protein; exposing the portion of protein to conditions that may alter the amount of the heavy element present in the portion of the protein and then measuring the x-ray fluorescence signal due to the heavy element; and subtracting the baseline x-ray fluorescence signal from the measured x-ray fluorescence signal.

DETAILED DESCRIPTION

Briefly, the present invention relates to using x-ray fluorescence (XRF) as a probe to determine binding selectivities of chemicals for receptors. The invention can also be used to estimate therapeutic index of a chemical. Another aspect of the invention relates to providing an estimate of the relative therapeutic indices of two chemicals.

An aspect of this invention is related to estimating the binding selectivity of a chemical to two or more receptors. The receptors are preferably proteins or other biological ligands. The receptors may be arrayed on a substrate. Arrays that include from about 2 to about 100,000,000 receptors, preferably from about 2 to about 1,000,000, and more preferably from about 2 to about 100,000 are especially useful with this invention.

Chemicals used with this invention generally include at least one element with an atomic number of nine or higher; these elements are referred to herein as "heavy elements".

Generally, a baseline XRF signal is established for a heavy element in each portion or aliquot of each receptor used with the invention. The baseline x-ray fluorescence signal may be calculated or measured.

After establishing the baseline XRF signal, the receptor(s) are exposed to one or more chemicals, preferably in solution, that are being tested for binding to the receptor(s). Exposure of the receptor(s) to the chemical(s) may or may not result in the formation of one or more complexes that are referred to herein as "chemical-receptor complexes". If an analog of the chemical is used, then the corresponding complex is referred to herein as an "analog-receptor complex". If the chemical is a drug, then the corresponding complex is referred to herein as "drug-receptor complex". Exposure of the receptor to the chemical/analog/drug allows such a complex to form, if it forms at all, under the conditions of temperature, elapsed time, presence of other chemicals or receptors, receptor concentration, chemical concentration, and other parameters.

After sufficient time has elapsed for one of the aforementioned complexes to form, the x-ray fluorescence signal due to the "heavy" element (e.g. phosphorus, chlorine, fluorine, sulfur, to name a few) in each chemical-receptor complex is measured.

After measuring the XRF signal due to the heavy element, the baseline X-ray fluorescence signal is subtracted from this measured x-ray fluorescence signal; the difference is referred to herein as the "net x-ray fluorescence signal". The net x-ray fluorescence signal is proportional to the amount of the chemical that is bound to the receptor in a chemical-receptor complex. Each net-x-ray fluorescence signal may be standardized by dividing by the amount of the receptor in the portion used for binding to the chemical. The amount of receptor typically may have units such as molecules, moles, moles per liter, grams, grams per liter, units of activity, and the like. If the same amount of receptor is used for each experiment, then each net x-ray fluorescence signal may be directly compared.

In addition, the net XRF signal should be standardized for the concentration of chemical if receptors are exposed to solutions having different concentrations of the chemical.

The standardized XRF signals obtained using this invention may then be compared in a variety of ways. One standardized x-ray fluorescence signal may be subtracted from another signal, for example. One standardized XRF signal may be divided by another signal. Preferably, when making comparisons among more than two signals, the signals are plotted on a graph so that comparisons among them may be easily visualized.

Another aspect of this invention is related to estimating the binding selectivity of at least two chemicals to two or more receptors and comparing their selectivities. For this aspect of the invention, each chemical must include at least one heavy element. The two or more chemicals may include the same heavy element or different heavy elements. The receptors, preferably proteins or other biological ligands, may be arrayed on a substrate. Arrays may include from about 2 to about 100,000,000 receptors, preferably from about 2 to about 1,000,000, and more preferably from about 2 to about 100,000. A measured or calculated baseline X-ray fluorescence signal would be obtained for the heavy element(s) in each portion or aliquot of each receptor used with the invention. After establishing the baseline X-ray fluorescence signal, the receptors are exposed to a plurality of chemicals, preferably in solution, which are being tested for binding to the receptors. Exposure of the receptors to the chemicals may or may not result in the formation of one or more complexes that are referred to herein as "chemical-receptor complexes". Exposure of the receptor to the chemicals allows such complexes to form, if they form at all, under the conditions of temperature, elapsed time, presence of other chemicals or receptors, receptor concentration, chemical concentration, and other parameters. After sufficient time has elapsed for one of the aforementioned complexes to form, the x-ray fluorescence signal due to the "heavy" element (e.g. phosphorus, chlorine, fluorine, sulfur, to name a few) in each chemical-receptor complex is measured. After measuring the x-ray fluorescence signal due to the heavy element(s), the baseline X-ray fluorescence signal is subtracted from this measured x-ray fluorescence signal; the difference is referred to herein as the "net x-ray fluorescence signal". The net x-ray fluorescence signal is proportional to the amount of the chemical that is bound to the receptor in a chemical-receptor complex. Next, each net x-ray fluorescence signal is standardized by dividing by the amount of the receptor in the portion used for binding to the chemical. The amount of receptor typically may have units such as molecules, moles, moles per liter, grams, grams per liter, units of activity, and the like. If the same amount of receptor is used for each experiment, then each net x-ray fluorescence signal may be directly compared. The standardized x-ray fluorescence signals may be compared in a variety of ways. One standardized x-ray fluorescence signal may be subtracted from another signal, for example. One standardized x-ray fluorescence signal may be divided by another signal. Preferably, when making comparisons among more than two signals, the signals are plotted on a graph so that comparisons among them may be easily visualized.

The invention also relates to drug manufacturing. The drug manufacturing process includes the determination of which chemical or chemicals bind to a type of receptor referred to in the art as a "druggable target," how strongly they bind, whether or not they bind selectively (i.e. whether or not they also bind undesirably to other receptors), and for those that bind selectively to what degree the selectivity is. After identifying a drug that binds strongly and selectively to a desired druggable target, the drug is synthesized in large quantities.

The invention can be used to estimate the binding selectivity of a chemical to one or more receptors under different conditions. For example, the binding affinity of a chemical in one solution can be compared to its binding affinity in a different solution. The chemical would include one or more heavy elements. The effect that other components that do not have a heavy element in either solution have on the binding affinity of the chemical could be inferred by observing any observed differences in binding affinity of the chemical.

Some aspects of the invention are related to personalized medicine, and involve estimating the relative effectiveness of two or more drugs. This may involve, for example, estimating the binding selectivities of two (or more) drugs to two (or more) receptors. The receptors may be proteins or other biological ligands, typically derived from a medical patient or a participant in a clinical drug trial. For medical patients, there may be a question about which drug to use to treat the patient, and the invention can be used to guide the doctor toward prescribing a specific drug for treatment. For applications related to personalized medicine, these types of drugs would include at least one heavy element. For drugs that are being compared, the drugs might include the same heavy element, or different heavy elements. Each drug may be a single chemical, or may be a mixture of chemicals. If the drug is a mixture of chemicals, then one of the active ingredients of the drug must have a heavy element.

An aspect of this invention is related to estimating the binding affinity of a chemical to one or more receptors, preferably proteins or other biological ligands that are arrayed on a substrate. The chemical would include at least one heavy element. First, a baseline XRF signal for the heavy element in each portion or aliquot of each receptor would be obtained, either by measuring or calculating the baseline signal. Afterward, the receptor(s) would be exposed to one or more chemicals. Chemicals that bind to the receptors result in the formation of chemical-receptor complexes that are detectable by measuring the XRF signal due to the heavy element in each chemical-receptor complex. This measured x-ray fluorescence signal is obtained by using x-ray excitation photons with an energy of at least 300 eV, which generate emission photons having a fluorescence lifetime that is less than the dead time of the x-ray detector. After measuring the x-ray fluorescence signal due to the heavy element, the baseline XRF signal is subtracted from this measured x-ray fluorescence signal, yielding the net XRF signal, which is proportional to the amount of the chemical that is bound to the receptor in a chemical-receptor complex. The net XRF signal would then be standardized. The standardized XRF signals may then be compared.

The invention can also be used to detect modifications in proteins. Examples of such detectable protein modification include, but are not limited to, post-translational modification of proteins, phosphorylation of proteins, and dephosphorylation of proteins. Detecting these modifications would typically begin by first establishing a baseline XRF signal for a heavy element in each portion or aliquot of each protein, and then exposing the protein to conditions that may result in protein modification. Afterward, the XRF signal due to the heavy element would be measured. The baseline X-ray fluorescence signal is then subtracted from this measured XRF signal, and the difference is the "net XRF signal". The net XRF signal would be standardized by dividing by the amount of the receptor in the portion being tested. The standardized XRF signals may then be compared.

This invention may be used to estimate the therapeutic index of a chemical/drug/analog. The therapeutic index is a measure of drug selectivity that is ordinarily calculated from data obtained from experiments with animals. The therapeutic index of the drug is typically defined as the ratio of two numbers, LD50/ED50, where LD50 is the dose of a drug that is found to be lethal (i.e. toxic) for 50 percent of the population of animals used for testing the drug, and ED50 is the dose of the drug that is found to have a therapeutic effect for 50 percent of that population. More broadly, it is a measure of the how much of the drug is needed to produce a harmful effect relative to the amount needed to produce a beneficial effect. The ratio LD50/ED50 is therefore, a measure of the approximate "safety factor" for a drug; a drug with a high therapeutic index can presumably be administered with greater safety than one with a low index. The invention may be used to provide an estimate of the therapeutic index by, for example, measuring the binding affinity of a chemical to a receptor associated with side effects and to a receptor associated with efficacy. The ratio of the measured binding affinities (efficacy divided by side effects) provides an estimate of the "therapeutic index". For an example of using DNA arrays with optical fluorescence high-throughput screening to estimate a therapeutic index, see R. Ulrich and S. H. Friend, "Toxicogenomics And Drug Discovery: Will New Technologies Help Us Produce Better Drugs?," *Nature Reviews Drug Discovery*, vol.1, pp. 84-88 (2002), incorporated herein by reference.

An example relating to the use of the invention to obtain a simple estimate of a therapeutic index may involve exposing an array of the proteins 5HT2A and NAa1 to a solution of olanzapine. Assuming that the 5HT2A and NAa1 of the array are present in equal amounts, the net sulfur XRF signal due to the olanzapine should be between 1.6 and 20 times higher for olanzapine bound to 5HT2A than for olanzapine bound to NAa1.

Another example relating to the use of the invention to obtain an estimate of a therapeutic index is now described. A therapeutic index for a non-steriodal anti-inflammatory drug (commonly referred to as an "NSAID") may be obtained by exposing an array that includes the proteins COX-1 and COX-2 to a solution of meloxicam. Assuming the COX-1 and COX-2 are present in equal amounts, the net XRF signal due to sulfur in the meloxicam should be about 10 times higher for meloxicam bound to COX-2 than for meloxicam bound to COX-1.

Yet another example relating to the use of the invention to obtain an estimate of a therapeutic index may involve exposing an array that includes COX-1, COX-2, and proteins derived from hepatocytes, to a solution of meloxicam. Assuming the COX-1 and COX-2 are present in equal amounts, the net XRF signal due to the sulfur in the meloxicam should be about 10 times higher for meloxicam bound to COX-2 than for meloxicam bound to COX-1. Any XRF signal due to sulfur in meloxicam bound to hepatocyte-derived proteins may suggest that the meloxicam may concentrate in the liver and may be cause for further analysis of the toxicity of meloxicam.

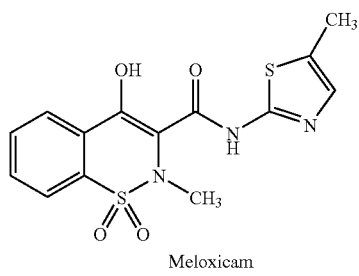 [SMILES: Cc1cnc(NC(=O)C2=C(O)c3ccccc3S(=O)(=O)N2C)s1]

Meloxicam

Binding selectivity information provided by the invention is important for understanding the properties of drugs. It is also important for other applications such as for medical diagnostics. For medical diagnostics, the ratio of the binding affinity of probe molecules (i.e. molecules that selectively bind to proteins associated with a particular disease) for a disease marker (i.e. a protein in a biological sample, such as a blood or sputum sample, from a patient having that disease, which indicates that a disease is present) vs. the binding affinity of probe molecules for other proteins not associated with that disease, is related to the accuracy of a medical test. If the probe molecules bind to the disease marker, then the medical diagnostic test provides a true positive result. However, when the probe molecules bind to other proteins besides the disease marker, then the medical diagnostic test provides a false positive result. The above ratio provides a measure of the true positive relative to the false positive, which is related to the accuracy of the medical test.

Diagnostic tests that use standard immunoassay methods require fluorescently-tagged chemicals. It has been previously pointed out that it is generally assumed that the attachment of a fluorescent tag to a chemical only serves to make visible the otherwise invisible chemical, and does not alter its binding properties. However, small changes to the structure of a chemical could affect its function, so this assumption that tagged chemicals have the same binding affinity and selectivity as their untagged counterparts may not be a valid one. The tagged chemicals are structurally different from their untagged counterparts, and these structural differences could affect their binding affinities and selectivities. Since binding affinities and selectivities derived using tagged chemicals are suspect, the binding properties of receptors and chemicals should be evaluated using the untagged chemical or receptor and not with a tagged chemicals. This is not possible with standard immunoassay methods, which require fluorescently-tagged chemicals. By contrast, the present invention allows an existing, untagged chemical (or analog or drug) to be used as the probe molecule.

An example of using the invention for a diagnostic test for inflammation, for example, may include exposing spatially separated proteins to a drug. Spatially separated proteins, for example COX-1 and COX-2 derived from a blood sample from a patient, may be exposed to the drug meloxicam. The binding affinities of meloxicam to COX-1 and COX-2 are known. Therefore, the net XRF signal due to sulfur in the meloxicam that is bound to COX-1 versus that for COX-2 may indicate the relative amounts of COX-1 and COX-2 in the blood sample.

The invention may also be used to develop optically fluorescent immunoassay diagnostics by comparing the selectivity of a non-fluorescently tagged chemical to a fluorescently-tagged chemical. XRF would be used to determine the binding selectivity of the non-tagged chemical, and either XRF or optical fluorescence would be used to determine the binding selectivity of the tagged chemical. If the selectivities of the tagged and untagged chemicals are proven to be similar, then the tagged-chemical may be used as the diagnostic with the expectation that its binding properties are acceptably similar to those of its untagged counterpart.

Binding selectivity information provided by the present invention is also important for uses related to Materials Science. Binding selectivity information can be used, for example, in designing high performance water filters, such as water filters that remove contaminants such as lead, arsenic, arsenate anions, or pesticides, from contaminated water. Water filters can be manufactured with receptors that have a high affinity for a particular contaminant (lead, for example) and a low affinity for other contaminants (iron, for example) in the contaminated water. By passing the contaminated water through this filter, the lead is removed while the iron isn't. The beneficial effect of not removing the iron is that the iron, which is present in much larger amounts than the lead is, does not overload the filter as the contaminated water is being treated. Overloading would mean that the filter would have to be replaced often.

The binding selectivity, i.e. the ratio of binding affinity of a chemical to one receptor versus the binding affinity to a different receptor, may be performed as follows. First, a baseline x-ray fluorescence is obtained. This baseline may be obtained by, for example, measuring the x-ray fluorescence (XRF) signal due to a particular element from each receptor in the absence of any added chemical. This is an empirical measurement that establishes the baseline XRF signal for that element for each receptor. Alternatively, the baseline XRF can be calculated for each receptor. This calculation requires knowledge of the amount of that element that is present in the receptor and a calibration factor to convert an amount of that element into an XRF intensity signal; the amount of the element believed to be present may then be multiplied by the calibration factor to provide a calculated XRF signal. The calibration factor may be obtained by measuring a set of standards containing that element, and calculating the signal as a function of the amount of the element. Preferably, the XRF baseline is a measured baseline.

For cases where there is a low probability that there is an element in common between the receptor and the chemical and where that element is used for the XRF measurement, a foreknowledge of the composition of the receptor(s) may be sufficient. For obtaining the XRF baseline for a set of organic receptors that are being screened for their binding affinities for a metal (e.g. lead) or for a chemical that has XRF-measurable chemical elements (e.g. phosphorus, chlorine) that are known not to be present in the set of organic receptors, for example, the baseline XRF signal of the receptors may be calculated or assumed to be negligible. For a sulfur-containing receptor (e.g. avidin) and a phosphorus-containing chemical (e.g. biotin-DHPE, or N-(Biotinoyl)-1,2-dihexadecanoyl-sn-glycero-3-phosphoethanolamine triethylammonium salt), for example, the XRF signal of phosphorus from the avidin may be assumed to be negligible, and any phosphorus XRF signal measured may be assumed to be due to the biotin-DHPE.

A receptor is preferably localized and separated from other receptors. Localization concentrates the receptor and any chemical bound to the receptor, therefore improving the sensitivity of the XRF technique. This sensitivity improvement due to localization for XRF contrasts with other techniques, such as optical fluorescence. Optical fluorescence may be affected by fluorescence quenching, fluorescent resonance energy transfer, photobleaching, and the like. Fluorescence quenching diminishes the optical signal and therefore decreases sensitivity. Fluorescence resonance energy transfer alters the wavelength of the fluorescence signal. Photobleaching degrades the fluorescence signal over time and exposure to light. By contrast, XRF is not subject to fluorescence quenching because the energy differences between the ground state and the excited states are much greater for XRF than for optical fluorescence. Energy loss via optical fluorescence may occur through non-radiative pathways that do not produce an optical signal. XRF sometimes is subject to fluorescence resonance energy transfer (see, for example, J. Sherman, *Spectrochimica Acta*, vol. 7, pp. 283-306 (1955)), incorporated by reference herein). Optical fluorescence usually requires an unsaturated functional group (a carbonyl group, a dienyl group, an aromatic group, etc.) with an electron that can be excited from the ground electronic state to an excited state with non-ionizing radiation (ultraviolet, visible, and near-infrared radiation). This excitation forms a reactive electron-hole pair that can chemically react with neighboring molecules, or within the same molecule. This chemical reaction degrades the optically fluorescent chemical functional groups, which diminishes the optical fluorescence during degradation. In contrast, XRF employs ionizing radiation for exciting inner core electrons of atoms. The chemical environment of the excited atoms does not have a significant effect on the XRF signal. Atoms are not degraded like chemical functional groups, so photobleaching does not occur in XRF.

When the chemical binds to a localized receptor, the chemical also becomes localized. In order to maximize the XRF efficiency, it is preferable that the dimensions of the receptor match those of the spot generated by the excitation beam.

For expensive receptors, it is preferable that the sample of receptor be as small as possible. It is therefore preferable that the receptor sample be localized within an area about 1 mm$^2$ or less, and within a volume of 1 mm$^3$ or less.

When multiple receptors are being tested, they are each deposited in separated portions on a substrate. The portions are spatially separated from each other so that the XRF excitation beam excites only one portion, and any chemical bound to the portion of receptor, at a time.

Receptor arrays such as analytical protein arrays, functional protein arrays, analytical DNA arrays, functional DNA arrays, analytical RNA arrays, functional RNA arrays, arrays derived from clinical patients, arrays derived from participants in clinical trials, tissue samples, tissue arrays, cellular arrays, and cellular samples may be used with the present invention. These and other types of arrays have been described in detail in the following papers: H. Zhu and M. Snyder, "Protein Chip Technology (Review)," *Current Opinion in Chemical Biology*, vol. 7, pp. 55-63, (2003); G. MacBeath and S. L. Schreiber, "Printing proteins as microarrays for high-throughput function determination," *Science*, vol. 289, pp. 1760-1763, (2000); E. T. Fung et al., "Protein biochips for differential profiling," *Current Opinion in Biotechnology*, Vol. 12, pp. 65-69, (2001); T. Kukar et al., "Protein Microarrays to Detect Protein-Protein Interactions Using Red and Green Fluorescent Proteins," *Analytical Biochemistry*, vol. 306, pp. 50-54, (2002); G. Y. J. Chen et al., "Developing a Strategy for Activity-Based Detection of Enzymes in a Protein Microarray," *ChemBioChem*, pp. 336-339, (2003); K. Martin et al., "Quantitative analysis of protein phosphorylation status and protein kinase activity on microarrays using a novel fluorescent phosphorylation sensor dye," *Proteomics*, Vol. 3, pp. 1244-1255, (2003); J. Burbaum and G. M. Tobal, "Proteomics in drug discovery," *Current Opinion in Chemical Biology*, Vol. 6, pp.427433, (2002); I. A. Hemmilä and P. Hurskainen, "Novel detection strategies for drug discovery," *Drug Discovery Today*, Vol. 7, pp. S150-S156, (2002). The arrays described in these papers may be used with the present invention.

In order to allow mass transport of a chemical to all parts of a receptor deposited on an area of the substrate, it is preferable that there be some inhomogeneity of the receptor in that deposited area. Regarding the inhomogeneity of the deposition, the amount of receptor on a 1 square micron portion of the deposited area should be different from the amount of receptor on another 1 square micron portion by at least 10 percent. An alternative way of comparing the amount of inhomogeneity of deposited receptor on an area involves measuring the amount of chemical in each 1 square micron pixel within the deposited area, finding the average amount of the chemical per square micron over the entire deposited area, and calculating the standard deviation of the amount of the chemical per square micron pixel. The standard deviation of the amount of the chemical per pixel divided by the average amount of the chemical per square micron of area should be greater than about 0.1% and preferably greater than about 1%.

Receptors may be inhomogeneously deposited by attaching the receptors to polystyrene beads, for example. The points of attachment on polystyrene beads are random and non-uniform. The attachment of receptors to beads is described in U.S. patent application 20030027129 entitled "Method for Detecting Binding Events Using Micro-X-ray Fluorescence Spectrometry," which was published on Feb. 6, 2003, which describes the use of beads that were about 80-120 micrometers in diameter, with an average diameter of about 100 micrometers.

The measured binding affinity of a chemical to a receptor depends on the chemical environment and temperature. More specifically, the binding affinity of a chemical to a receptor does not change when the chemical environment does not change. External factors, however, may have an effect on the measured binding affinity.

The free energy of binding of a chemical to a receptor may be represented by the following equation:

$$\Delta G = \Delta H - T\Delta S$$

where $\Delta G$ is the change in the Gibbs free energy of the binding reaction, $\Delta H$ is the change in enthalpy of the binding reaction, T is the temperature, and $\Delta S$ is the change in entropy of the binding reaction (see, for example: Gordon M. Barrow, Physical Chemistry, $5^{th}$ Ed., McGraw-Hill, N.Y., 1988, Chapter 7). The temperature should be constant to avoid changing the $T\Delta S$ term, because changes to the $T\Delta S$ term would introduce temperature derived artifacts into the measurements. $\Delta G$ will also be affected by, for example, the presence of materials that coordinate to the receptor and/or chemical. Bonds that form between these materials and the receptor and/or chemical must be broken before the chemical can bind to the receptor. Energy is required to break these bonds, and this energy will be factored into $\Delta G$ of the equation, and will make $\Delta G$ of binding between the chemical and receptor appear smaller than it actually is. Therefore, in order to obtain binding affinities for a chemical with multiple receptors, the chemical environment for the receptors and chemicals should not change. In addition, the temperature should not vary between measurements and all measurements should be taken at substantially the same temperature, i.e. within ±3° C., and more preferably within ±1° C.

For drug development, the chemical environment preferably approximates that of the physiological environment. Useful drugs should perform optimally at, or near, physiological temperatures. One aspect of this invention is related to determining binding selectivities at or near the temperature of the body, which is about 37 degrees Celsius. Preferably, the exposure of receptors to chemicals/analogs/drugs according to this invention is typically performed at a temperature of from about 15 degrees Celsius and about 45 degrees Celsius, and more preferably is between 32 degrees Celsius and 42 degrees Celsius, and most preferably at a temperature of about 37 degrees Celsius.

Useful drugs should also perform optimally in the presence of other, potentially interfering chemicals that are also present in a physiological environment. The therapeutic index provides an estimate of the performance of a drug. Simple estimates of a therapeutic index may be obtained for a chemical in a solution that does not contain potentially interfering chemicals. More realistic estimates of the therapeutic index are obtained when the chemical is in an environment that more closely approximates biological conditions. An example of such an environment is a buffered solution that contains chemicals that are typically found in biological organisms (e.g. blood-borne ligands).

For medical purposes, such as the development of new therapeutic chemicals (i.e. drugs), the ratio of the binding affinity of a chemical to the target receptor versus the binding affinity of that chemical to one or more other receptors (which is an estimate of the therapeutic index according to the present invention) is important to know. It is also important to know the binding affinity and the therapeutic index estimate of the chemical for these receptors in typical chemical environments and in the presence of common biological ligands. The binding affinity may be measured in the presence of, for example, blood-borne proteins, ligands, fats, triglycerides, and fatty acids. These proteins and ligands may function as a proxy for distribution of the chemical between the circulatory system and cells. Fats, triglycerides, and fatty acids may function as a proxy for the distribution of the chemical between fat cells (or cell membranes) and the target receptor, as well as for passive transcellular transport.

Another aspect of the present invention is related to determining whether or not a first chemical and a second chemical have similar selectivity for binding to each of a plurality of receptors. For example, if a baseline is obtained for receptor 1 and receptor 2, and then if chemical A and chemical B and chemical C are exposed to receptor 1 and receptor 2, and the baseline is subtracted from the XRF signals after exposure, the similarity of the binding selectivities can be assessed. For this example, chemical A and chemical B are both are selective for Receptor 1 versus Receptor 2 by about an order of magnitude, while chemical C is not selective for Receptor 1 versus Receptor 2, as shown in TABLE 2 below.

TABLE 2

|  | Receptor 1 | Receptor 2 |
| --- | --- | --- |
| Chemical A | 10 | 1 |
| Chemical B | 11 | 1 |
| Chemical C | 1 | 1 |

This aspect of the invention may be exemplified with specific receptors having known properties. For example, Receptor 1 may be exemplified by COX-1 (inhibition of which is associated with intestinal ulcers) and Receptor 2 may be exemplified by COX-2 (inhibition of which is associated with anti-inflammation).

TABLE 3 below includes selectivity data for sample canine COX-1 and COX-2 (see, for example: "Christopher Jones, Practical COX-1 and COX-2 Pharmacology: What's it All About?," which can be found at the website www.vetmedpub.com/cp/pdf/symposium/nov1.pdf).

TABLE 3

|  | COX-1 | COX-2 |
| --- | --- | --- |
| Celecoxib | 1 | 9 |
| Meloxicam | 1 | 10 |
| Ketoprofen | 1 | .6 |
| New Drug (goal) | 1 | >10 |

TABLE 3 compares the selectivity of CELECOXIB, MELOXICAM, and KETOPROFEN for the receptors COX-1 and COX-2. According to TABLE 3, CELECOXIB has a selectivity of 9 to 1 in favor of COX-2 versus COX-1, and MELOXICAM has a selectivity of 10 to 1 also in favor of COX-2 versus COX-1, while KETOPROFEN has a selectivity in favor of COX-1 versus COX-2 of only 1 to 0.6. Drug development involves finding/developing new drugs that have superior selectivities (i.e. superior therapeutic indices) versus existing drugs. The discovery/development of more selective drugs than those shown in TABLE 3 may involve measuring the selectivity of a new drug and comparing its selectivity to that of the more effective drugs e.g. CELECOXIB. The goal would be to develop a new drug with superior selectivity for COX-2 over COX-1 as compared to CELECOXIB.

A new drug should be at least one percent more selective, and more preferably more than 5 percent more selective than an existing, effective drug.

An example that demonstrates how the present invention may be used to provide information related to the selectivity of a plurality of receptors to a chemical is now described. The chemical is the lead ion. For this example, a library consisting of 400 tripeptide receptors was prepared by split-pool synthesis. Each receptor of the library was covalently attached to a spherical polystyrene resin particle. The particles had an average size of about 100 microns. The library of receptors was exposed to an aqueous solution, having a pH of 7, of lead nitrate (7 mM). A portion of the library of receptors was then analyzed by XRF. The XRF intensity and relative binding affinity of three of the receptors for lead ion are shown in TABLE 4 below.

TABLE 4

| Receptor | Pb XRF Signal | Relative Binding Affinity |
|---|---|---|
| Receptor 4.1 | 991.93 | 1.11919349 |
| Receptor 4.2 | 924.94 | 1.04360875 |
| Receptor 4.3 | 886.29 | 1 |

Another example that demonstrates how the present invention may be used to provide information related to the selectivity of a plurality of receptors to two chemicals is now described. The two chemicals are the lead ion and the iron ion. For this example, a library consisting of 400 tripeptide receptors was prepared by split-pool synthesis. Each receptor of the library was covalently attached to a spherical polystyrene resin particle. The particles had an average size of about 100 microns. The library of receptors was exposed to an aqueous solution (pH 7) of lead nitrate (7 mM) and iron nitrate (7 mM). A portion of the receptors was then analyzed by XRF. The XRF intensity and relative binding affinity of two of the receptors for lead ion and iron ion are shown in TABLE 5 below.

TABLE 5

|  | Pb XRF Intensity | Fe XRF Intensity | Pb XRF Intensity/ Fe XRF Intensity |
|---|---|---|---|
| Receptor 5.1 | 2295 | 505 | 4.54 |
| Receptor 5.2 | 13092 | 252 | 51.95 |

The first entry of TABLE 5 relates to data obtained for the receptor labeled receptor 5.1, and the second entry relates to XRF data obtained for the receptor labeled receptor 5.2. The Pb XRF intensity of receptor 5.1 is 2295, the Fe XRF intensity, is 505, and the ratio of Pb XRF intensity to the Fe XRF intensity, which indicates the selectivity of receptor 5.1 for binding to lead versus binding to iron, is 4.54. Similarly, the Pb XRF intensity for receptor 5.2 is 13092, the Fe XRF intensity is 252, and the ratio of the Pb XRF intensity to the Fe XRF intensity is 51.95. The ratio of 51.95 to 4.54, which equals 11.4, indicates that receptor 5.2 is 11.4 times as selective for lead than receptor 5.1 is.

For drug development, it is desirable to understand how the drug will bind to a receptor. Drug development may involve systematically varying the chemicals being tested for their affinities to one or more receptors, in order to optimize the binding affinity of one of these chemical analogs to a desired receptor-and to optimize the therapeutic index, i.e. the ratio of the affinity of the chemical to a desired receptor to the affinities of that chemical to undesired receptors. This systematic variation of chemicals for drug development is sometimes referred to as a drug development analog program. The development of a potential new drug using analogs and XRF according to the present invention involves determining the binding affinity of a potential drug to multiple receptors, and comparing these binding affinities to provide selectivity information. This process is completed for a first chemical, and then completed for a second chemical that is an analog of the first chemical. Then the binding affinities and selectivities for the first chemical and for its analog are compared to determine which of the two is the more selective. This may involve mixing the first chemical with one or more receptors, allowing a receptor-chemical complex to form, and then measuring the amount of receptor-chemical complex formed using XRF, then repeating these steps with the analog. Any complexes that form with the analog would also be measured by XRF. This may be repeated with additional analogs of the first chemical.

There are several criteria that may be used to determine whether chemicals are analogs of the first chemical. One criterion is whether the first chemical and another chemical have one or more properties in common. The similarity may be determined by computational modeling, such as a "Quantitative Structure Activity Relationship" (QSAR, see, for example: R. Perkins et al., "Quantitative Structure-Activity Relationship Methods: Perspectives on Drug Discovery and Toxicology," *Environmental Toxicology And Chemistry*, vol. 22, pp.1666-1679 (2003); and T. W. Schultz et al., "Quantitative Structure-Activity Relationships (QSARs) in Toxicology: a Historical Perspective" *THEOCHEM*, vol. 622, pp.1-22 (2003), both incorporated by reference herein).

QSAR models compare the charge, polarity, hydrogen-bonding donor/acceptor pattern, lipophilicity, volume, and other properties of chemicals to determine whether two or more chemicals are likely to have similar binding properties for a receptor.

Another criterion for determining whether two chemicals are analogs of each other relates to whether the two chemicals have a common functional group and where that functional group is attached. The following clarifies what is meant by the term analog. Benzene, methylbenzene, ethylbenzene, isopropylbenzene, and n-propylbenzene, for example, are analogs of each other. Olanzapine and trifluoromethylolanzapine are analogs of each other. Methyl salicylate, ethyl salycylate, phenyl salicylate, N-methyl salicylamide, N,N-dimethylsalicylamide, and salicylic acid are analogs of each other. The aromatic compounds 4-chlorotoluene and 3-chlorotoluene are analogs of each other. Cyclopentane, cyclohexane, and cycloheptane are analogs of each other. Benzene, pyridine, and thiophene are analogs. Ethyl benzene and methoxybenzene are analogs of each other. Ethyl benzene, ethenyl benzene (i.e. styrene), and ethynyl benzene (i.e. phenyl acetylene) are analogs of each other. More generally, enantiomers of a chemical are analogs of each other; diastereomers are also analogs of each other.

A third criterion for determining whether two chemicals are analogs is related to whether the two chemicals share atoms having the same connectivity, where the term connectivity is meant to describe the shortest path of atoms that connect two functional groups. For example, 1,2-diclorobenzene and 1,2-dinitrobenzene have the same connectivity between the two functional groups; the connectivity between the chlorine groups in the chemical 1,3-diclorobenzene is the same as the connectivity between the two nitro groups in the chemical 1,3-dinitrobenzene.

Preferably, a chemical being tested for binding with a receptor according to the present invention includes at least one chemical element having an atomic number of nine or higher. Excitation photons used with the present invention should have energies of at least 300 eV. The excited atoms should have a fluorescence half-life of 10 ns or less. The importance of having such a short fluorescence lifetime is related to the "dead time", which is a period of time after the x-ray fluorescence is measured. No additional x-ray fluorescence can be measured during the dead time. Preferably, the fluorescence lifetime of the type of atom being measured should be less than the dead time of the detector. More preferably, the fluorescence being measured should have a fluorescence half-life of 10 nanoseconds (ns) or less, and most preferably the fluorescence being measured should have a half-life of 100 picoseconds (ps) or less.

If a mixture of chemicals, as opposed to a single chemical, is used, only one of the chemicals is required to have a heavy element. If more than one has a heavy element, and the heavy element is the same element, then a baseline XRF measurement of the binding affinity of each of the chemicals with that element to one or more receptors should be obtained. The measurements may be obtained sequentially, e.g. by measuring the XRF spectrum of each receptor of an array, then exposing the receptors of the array to a chemical, then measuring the XRF spectrum of the array after exposure to the chemical, then adding another chemical, then measuring the XRF spectrum of the array after exposure to the other chemical. This process may be repeated for as many chemicals as desired.

After measuring binding affinities between receptors and chemicals, the receptors may be analyzed in terms of any of their particular structural or functional features than may promote binding or inhibit binding. A variety of analytical techniques useful for performing this type of analysis include spectroscopy (e.g. infrared spectroscopy, fluorescence spectroscopy), spectrometry (e.g. mass spectrometry, nuclear magnetic resonance spectrometry, surface plasmon resonance), functional assays, and the like.

The binding properties of a receptor to a chemical may be correlated with a positive, or with an adverse, response of an animal, clinical trial participant, or medical patient. For the case of clinical trial participants, for example, those participants who respond adversely to the drug candidate may have a different receptor affinity or selectivity than participants that respond positively to the drug candidate.

One aspect of the invention may be demonstrated using an array prepared as described in Kukar et al., "Protein Microarrays to Detect Protein-Protein Interactions Using Red and Green Fluorescent Proteins," *Analytical Biochemistry*, vol. 306, pp. 50-54 (2002). The baseline sulfur content of the receptors of the array would be measured using x-ray fluorescence spectroscopy. Afterward, the receptors of the array would be exposed to a solution of olanzapine, which has the structural formula

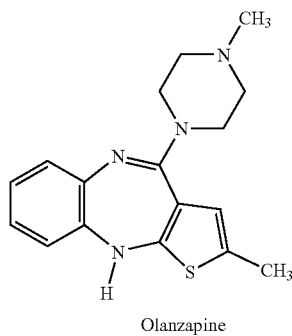 [SMILES: Cc1cc2c(s1)Nc1ccccc1N=C2N1CCN(C)CC1]

Olanzapine and the chemical formula $C_{17}H_{20}N_4S$ (olanzapine is the active ingredient in ZYPREXA®). Afterward, the sulfur content of each receptor would be measured again using x-ray fluorescence microscopy. The difference in sulfur content between the two measurements is related to the binding of olanzapine to receptors the array.

It is believed that the therapeutic effects of olanzapine are a result of olanzapine binding to several receptors, including the human serotonin 5HT2A receptor (see, for example: www.gpcr.org) [embedded hyperlink deleted]. Toxic effects are believed to occur as a result of olanzapine binding to alpha-1-adrenergic (NAa1) receptors (see, for example: "Olanzapine (Zyprexa®)" in Clinical Toxicology Review, vol. 18, no. 2, March 1997. The pKi (where pKi=-log Ki, where Ki is the inhibition equilibrium constant) of olanzapine for 5HT2A is reported to be 7.8-8.9, while the pKi of olanzapine for NAa1 is reported to be 6.3-7.6. If the binding of the chemical to a receptor also inhibits that receptor, then the pKa and the pKi of the chemical have the same value.

The selectivity of binding of olanzapine to NAa1 versus 5HT2A may be measured by first preparing an array of NAa1 and 5HT2A on a substrate, then measuring the baseline sulfur content of each enzyme using XRF, then contacting the arrayed enzymes with a solution of olanzapine, and then measuring the total amount of sulfur using XRF, and then subtracting the baseline amount of sulfur from the total amount of sulfur, which indicates the amount of olanzapine that binds to each enzyme.

From the binding data obtained for olanzapine, it appears that chemicals useful as drugs form a complex with at least one receptor that has a pKi of greater than 5.

According to the invention, the x-ray excitation beam is used to excite one receptor at a time. The temperature of the array should be kept constant so that each x-ray measurement is performed at the same temperature, or at nearly the same temperature (±3 degrees Celsius). For the case of measuring the binding of olanzapine to each receptor, for example, each measurement should be performed at the same temperature or at nearly the same temperature because the binding affinity changes as the temperature changes.

After the selectivity of the olanzapine for binding to 5HT2A and to NAa1 is measured, additional chemicals can be similarly measured in order to determine whether any other chemical has a better selectivity for 5HT2A versus NAa1. A chemical such as the trifluoromethylolanzapine, which has the structural formula

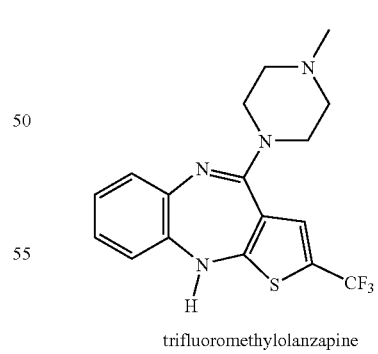

trifluoromethylolanzapine for example, may be screened against the same receptor array, or screened against another receptor array having the same proteins, and the binding selectivity for trifluoromethylolanzapine can be measured If the selectivity of trifluoroolanzapine for 5HT2A versus NAa1 is greater than the selectivity of olanzapine is, then trifluoromethylolanzapine would be expected to be a superior drug.

Another aspect of the present invention relates to the determination of the kinetic parameters of an interaction between a chemical and a receptor.

After the baseline is measured or calculated for a receptor, as previously described, the receptor is exposed to a chemical at a particular temperature. The temperature is preferably a fixed temperature, preferably between about 27 degrees Celsius and about 47 degrees Celsius and more preferably is a fixed temperature between about 32 degrees Celsius and about 42 degrees Celsius. The XRF signal of any receptor-chemical complex formed is then measured. After taking this measurement at a first fixed temperature, the temperature is adjusted so that it is different from the first temperature by at least 2 degrees Celsius. The XRF signal should then be measured for the sample at this new temperature.

Alternatively, the first measurement and second measurement can be performed as follows. The receptor and chemical can be mixed first at one temperature, and next at a different temperature. Then, the chemical-receptor complexes that form are isolated (e.g. by spatially separation) so that any chemical that was bound to the receptor remains spatially associated with the receptor. The XRF measurements may then be obtained at any temperature desired.

The kinetic parameters for the formation of a receptor-chemical complex may similarly be determined by obtaining the baseline XRF signal for at least one receptor as described above, followed by exposing the receptor to a first solution of a chemical where the chemical is present in a fixed concentration. The XRF signal of any chemical-receptor complex is then measured. These steps are then repeated with a second solution having a different concentration of the chemical. The contact times between the first solution and the receptor and the second solution and the receptor are measured in order to determine the rate of the binding reaction, which is related to the amount of complex formed per unit time. Preferably the contact times between the first solution and the receptor and the second solution and the receptor are the same.

The method may also be practiced using a solution having a concentration gradient; using a concentration gradient is similar to using two solutions at two different times. The reaction kinetics may then be determined, as described in Gordon M. Barrow, Physical Chemistry, 5$^{th}$ Ed., McGraw-Hill, N.Y., 1988, chapter 18. The activation parameters $\Delta G^{\neq}$, $\Delta H^{\neq}$, $\Delta S^{\neq}$ may be determined using the Arrhenius equation (see, for example: Gordon M. Barrow, Physical Chemistry, 5$^{th}$ Ed., McGraw-Hill, N.Y., 1988, pp. 710-712.) and the Eyring equation (see, for example: Gordon M. Barrow, Physical Chemistry, 5$^{th}$ Ed., McGraw-Hill, N.Y., 1988, pp. 756-757.)

This aspect of the invention may be demonstrated by preparing a protein array that includes at least one protein receptor (see, for example: Kukar et al., "Protein Microarrays to Detect Protein-Protein Interactions Using Red and Green Fluorescent Proteins," *Analytical Biochemistry*, vol. 306, pp. 50-54 (2002), incorporated herein by reference). The baseline sulfur content of the protein spots of the array is determined using x-ray fluorescence spectroscopy. After determining the baseline sulfur content, the protein array is contacted with a solution of olanzapine. Afterward, the sulfur content of each protein spot is determined again using x-ray fluorescence microscopy. The difference in sulfur content between the two measurements for each protein spot is then quantified. This difference is related to the binding of olanzapine to proteins in the array.

In order to measure the rate of binding of olanzapine to 5HT2A, a solution of olanzapine may be contacted with a 5HT2A. The 5HT2A may be in solution, or as part of an array of proteins, or associated with a substrate. If the 5HT2A is in solution, it should be immobilized in some manner, such as in the manner described in U.S. patent application Ser. No. 10/621,825 entitled "Method and Apparatus for Detecting Chemical Binding". Any increase in the sulfur XRF signal, which is presumably due to an increase in the amount of olanzapine that is bound to 5HT2A, may be measured periodically over time to determine the rate at which olanzapine binds to 5HT2A. This may be repeated using solutions having various concentrations of olanzapine, and at different temperatures in order to determine the rate of binding at different temperatures; this is important for determining the activation parameters $\Delta G^{\neq}$, $\Delta H^{\neq}$, $\Delta S^{\neq}$, as well as for determining the binding kinetics that would be expected for a healthy patient (37° C.) versus a patient with a mild (38° C.) or severe (>38° C.) fever.

For examining a chemical that is a candidate for drug discovery according to the present invention, it is preferable that the chemical has one or more features that have come to be known as "Lipinski" features, described in C. A. Lipinski et al., "Experimental And Computational Approaches To Estimate Solubility And Permeability In Drug Discovery And Development Settings," *Advanced Drug Delivery Reviews*, vol. 23, pp. 3-25, (1997). These features include the following: a molecular weight equal to or less than about 500 daltons; a number of hydrogen bond acceptors that is equal to five or less; a number of hydrogen bond donors that is equal to ten or less; and a logP of five or less where P is the ratio of the solubility of the chemical in octanol to the solubility of the chemical in water. Elaborating on the hydrogen bond acceptor properties of drug candidates, it is preferable that the chemical has the property that the sum of nitrogen, oxygen, sulfur, fluorine, chlorine, bromine, and iodine groups available for hydrogen bonding in the chemical is five or less. For the purposes of counting hydrogen bond acceptors, each of the following is counted as a single hydrogen bonding acceptor: difluoromethyl groups, trifluoromethyl groups, dichloromethyl groups, trichloromethyl groups, dibromethyl groups, tribromethyl groups, ester groups, amide groups, carboxylic acid groups, urea groups, and carbamate groups. Also for the purposes of counting hydrogen bond acceptor groups, the following are not counted as a hydrogen bond acceptor: nitro groups, nitroso groups, and cyano groups.

While the Lipinski features suggest that a molecular weight of less than about 500 is preferable, Hemmilä (vide infra) reported that chemicals having a molecular weight of 5000 daltons or less cannot be tagged with an optical tag without overly perturbing their binding properties, such as binding affinities (see I. A. Hemmilä and P. Hurskainen, "Novel detection strategies for drug discovery," *Drug Discovery Today*, Vol. 7, pp. S150-S156, (2002)). The present invention does not employ tags and thus can be used for studying the binding of chemicals that have a molecular weight of 5000 daltons or less.

For a chemical having hydrogen bond donor groups, it is preferable that the chemical has the property that the sum of hydrogen atoms bound to sulfur, nitrogen, and oxygen in the chemical is ten or less.

For drug candidates, it is preferable that chemical is soluble in water. The chemical should be dissolved in a fluid that includes water, preferably with a pH of from about pH 6 to about pH 8.

The chemical may have zero, one, or more than one chiral center. A chemical sample that contains equal amounts of each enantiomer may be used. Once it has been determined using the invention that the chemical binds to a receptor, the chemical may be analyzed to determine which particular enantiomer, if any, is bound to the receptor. For the case of more than one enantiomer binding to the receptor, it may be determined which is bound more strongly to the receptor. It is important to determine which receptor(s) bind to each enantiomer of the chemical in order to identify any potential side effects of a toxic enantiomer. Thalidomide, for example, is a chemical that was used to treat morning sickness until it was discovered that a toxic enantiomer of the chemical was responsible for birth defects.

In order to optimize the balance between the speed of analysis versus the sensitivity of the XRF technique, it is preferable that a sample of receptor, or chemical-receptor complex, be exposed to the X-ray excitation beam for a period of time from about 100 milliseconds to about 600 seconds. To further optimize speed versus sensitivity, it is preferable that the x-ray excitation beam spends more time focused on a pixel that contains receptor and/or receptor-chemical complex than on a pixel that is substantially devoid of receptor or receptor-chemical complex. This way, less time is wasted analyzing parts of a sample that have little useful information.

An x-ray translucent barrier may be used with a receptor or receptor array in order to minimize evaporation and evaporative cooling of receptors and/or chemicals.

Another aspect of the present invention relates to use for personalized medicine. Personalized medicine is described in "Personalized Prescribing," The Scientist, 15[12]:10, Jun. 11, 2001, incorporated herein by reference. Personalized medicine is important because it is expected to decrease the number of adverse drug reactions, which currently result in the deaths of about 100,000 hospitalized patients per year, and cause serious side effects in another 2.2 million people. Personalized medicine currently relies on genotyping a patient in order to guide the physician in administering drugs to the patient. This genotyping focuses on single nucleotide polymorphism (SNP) analysis. The cost per SNP analysis currently is about 1 dollar per SNP, but with the current poor understanding of pharmacogenomics and the large number of possible SNP's (thousands), it is believed that costs related to SNP analysis must decrease to pennies per SNP before SNP analysis becomes more widely used. The analysis provided using the present invention, by contrast, allows phenotyping and direct analysis of drug interactions with protein profiles, thus providing higher quality information about the particular patient and disease Thus, the present invention may be used in personalized medicine to assist physicians in prescribing drugs for their patients. A protein array, such as an array on a commercially available protein chip manufactured by Ciphergen™ or Zyomyx™, for example, may be exposed to protein extracts from a cancer patient. In this case, as in others where there is a clear difference between diseased tissue and healthy tissue, extracts from the tumor and from healthy tissue would be taken from the patient. After exposing the chip to the extracts, a baseline XRF baseline spectrum would be obtained. Solutions of each drug that the doctor is considering for treating the tumor would then be contacted with the protein chip. The binding affinity of each drug would then be measured according to the invention, which involves measuring the XRF signals for heavy elements present in the drug-receptor complex, subtracting out the baseline from this measurement, and then comparing the signals to see which drug exhibits a more selective binding to the tumor versus the healthy tissue and/or which drug binds more strongly to the tumor.

The efficacy of a drug may be correlated with the binding affinity of the drug for diseased tissue; more efficacious drugs tend to bind more strongly to proteins associated with a disease than less efficacious drugs do. Side effects of a drug may be correlated with the ability of the drug to bind to healthy tissue. The choice of which drug to prescribe may be based on the ability of the drug to bind strongly to the diseased tissue (or to proteins associated with the diseased tissue) and to bind weakly, or not at all, to healthy tissue (or to proteins associated with health tissue). A cancer biopsy sample (i.e. from a tumor), for example, may be lysed and arrayed on an analytical protein chip. The chip would then be exposed to a variety of chemotherapy drugs (or even cold radiopharmaceutical surrogates) and the relative binding affinities of the different drugs to the arrayed biopsy sample would guide the course of treatment. Side effects could be quantified and minimized by performing a similar assay using non-cancerous tissue, and selecting the drug based on minimized drug-enzyme interactions. This method may also be used with drug mixtures, which are sometimes referred to as "cocktails".

The invention may be used for participant stratification in clinical trials of proposed drugs. Currently, participant stratification methods are based on DNA chips, where genomic profiles are correlated with the variation in participant response to chemicals (e.g. drug candidates). The correlation of genomic profiles with patient response is sometimes referred to as "pharmacogenomics". Genomic profiles are several steps removed from the proteomic profile of a participant in a clinical trial of a drug; genetics and environmental factors affect which proteins are expressed. Drugs regulate protein behavior, and so the protein make-up of a particular participant and how those proteins interact with the drug(s) in a course of clinical trials will provide the best information for participant stratification. Protein chips have become inexpensive and commercially available.

Regarding the use of the invention for participant stratification in a clinical trial of a drug such as an anti-cancer drug, a protein array on a protein chip may be exposed to protein extracts from a cancer patient, as described above. Protein extracts of the tumor and of healthy tissue would be taken from the patient. After exposing the chip to the extracts, a baseline XRF baseline spectrum would be obtained. Solutions of each drug being tested in the trial would then be contacted with the protein chip having the bound proteins. The binding affinity of each drug would then be measured according to the invention, which involves measuring the XRF signals of heavy elements present in the drug-receptor complex, subtracting out the baseline from this measurement, and then comparing the signals to see which drug exhibits a more selective binding to the tumor versus the healthy tissue and/or which drug binds more strongly to the tumor. This information may then be correlated to the efficacy, toxicity, and side effects of the drugs as measured in the clinical trials. The importance of clinical trial stratification is that if a drug can be shown to only have unacceptable side effects for people with specific genomic and/or proteomic profiles (i.e. a strata), the drug may be approved for other strata for which the drug has acceptable side effects. This process may allow drugs that would otherwise be rejected by the Food and Drug Administration or other regulatory agencies to be accepted for a more limited use, thereby allowing drug candidates to be used that would otherwise be rejected.

Another aspect of the invention relates to drug manufacturing. The drug manufacturing process is lengthy, typically including a period of time where a new drug is discovered, another period of time where the drug is developed, more time where the drug is tested with animals and then humans, and more time where the drug is synthesized on a larger and larger scale. Discovery involves determining which chemicals are likely to be effective drugs, and is often conducted by measuring the interaction between a chemical and a receptor (sometimes referred to in the art as a "druggable target"). Development involves in vitro testing to estimate the likely side effects and pharmacokinetics of a chemical. Animal testing is used to determine whether the drug is safe in animals, and are sometimes used to determine whether a drug is effective in animals. If the drug is deemed sufficiently safe in animals, it may be administered to human volunteers in clinical trials to determine human safety and efficacy. If a drug is deemed safe and effective in human volunteers, it may be mass-produced for use by physicians and patients. All of these steps are necessary.

The invention may be used to estimate the efficacy of a chemical (analog, drug). Measuring the affinity of one or more chemicals for a druggable target fulfills the discovery step.

The invention may be used to estimate side effects and/or pharmacokinetics by measuring the binding selectivity of one or more chemicals for a druggable target versus other proteins that may be associated with side effects or pharmacokinetics. Animal studies and human studies may then be performed, followed by mass production of the drug using chemical synthesis or biological synthesis.

Another aspect of the invention relates to its use in measuring post-translational modification of proteins, such as the phosphorylation or dephosphorylation of one or more proteins. Phosphorylation and desphosphorylation reactions are described by K. Martin et al. in "Quantitative Analysis Of Protein Phosphorylation Status And Protein Kinase Activity On Microarrays Using A Novel Fluorescent Phosphorylation Sensor Dye," *Proteomics*, vol. 3, pp. 1244-1255 (2003). This paper describes the need for radioactive labeling and fluorescent tagging; however, both radioactive labeling and fluorescent tagging are unnecessary in view of the present invention, which can measure the amount of phosphorus directly in an untagged protein using XRF.

An example of the use of the invention for measuring post-translational modifications may include establishing a baseline X-ray fluorescence signal for a heavy element (i.e. an element having an atomic number of nine or greater), such as phosphorus, in a portion of a protein. The portion of protein is then exposed to reaction conditions such as those described by K. Martin et al. in "Quantitative Analysis Of Protein Phosphorylation Status And Protein Kinase Activity On Microarrays Using A Novel Fluorescent Phosphorylation Sensor Dye," *Proteomics*, Vol. 3, pp.1244-1255, (2003), which alter the amount of phosphorus in the protein. The x-ray fluorescence signal due to the element would then be remeasured using XRF. Subtracting the baseline x-ray fluorescence signal from the remeasured x-ray fluorescence signal provides a net X-ray fluorescence signal that may be correlated with the amount of the element in the protein, which provides an estimate of the extent of phosphorylation of the protein.

The following EXAMPLES provide an illustration of various aspects of this invention.

EXAMPLE 1

Binding of ziprasidone to protein receptors. A protein array may be prepared as described in G. MacBeath and S. L. Schreiber, "Printing Proteins As Microarrays For High-Throughput Function Determination," *Science*, vol. 289, pp. 1760-1763, (2000). This protein array may be exposed to a solution of ziprasidone, which is the active ingredient in the drug Geodon™. Ziprasidone has a molecular formula of $C_{21}H_{20}ClN_4OS$ and the structure shown below.

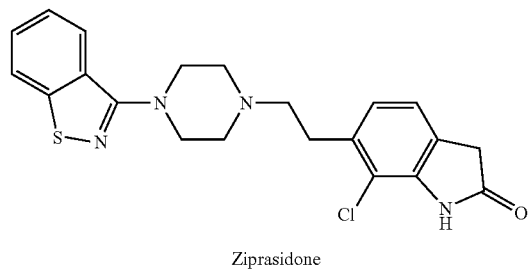 [SMILES: O=C1Cc2ccc(CCN3CCN(c4nsc5ccccc45)CC3)c(Cl)c2N1]

Ziprasidone

The elements chlorine and sulfur may each be detected by x-ray fluorescence. After the array is exposed to the ziprasidone-containing solution, an EDAX Eagle Microprobe x-ray fluorescence microscope, for example, could be used to determine the receptor proteins that bind to the ziprasidone. The amount of ziprasidone that is associated with each receptor may be quantified by x-ray fluorescence.

None of the proteins of the array are expected to contain the element chlorine, so the chlorine x-ray fluorescence baseline may be assumed to be zero (although the chlorine x-ray fluorescence baseline could be measured). At least some of the proteins are expected to contain the element sulfur (from sulfur containing amino acids such as cysteine and methionine). Before exposing the array proteins to ziprasidone, a baseline X-ray fluorescence signal for sulfur may be obtained, and after exposure to the ziprasidone, the X-ray fluorescence signal due to sulfur would be measured again. The difference in the sulfur signals would be used to determine whether any receptor-ziprasidone complex formed, and measuring the amount of any such complex that formed.

EXAMPLE 2

Binding of ziprasidone to DNA receptors. A DNA array such as an Affymetrix GeneChip™ may be exposed to a solution that contains ziprasidone, as described in EXAMPLE 1. After the array is exposed to the ziprasidone-containing solution, an EDAX Eagle Microprobe x-ray fluorescence microscope, for example, could be used to determine the locations of those receptor DNA that bind to the ziprasidone. The amount of ziprasidone that is associated with each receptor may be quantified by x-ray fluorescence.

None of the DNA receptors of the array are expected to contain the elements chlorine or sulfur, so the chlorine X-ray fluorescence baseline and the sulfur X-ray fluorescence baseline may be assumed to be zero. After exposure to the ziprasidone-containing solution, the X-ray fluorescence signal due to sulfur and/or chlorine would be measured. The measured X-ray fluorescence signal(s) may be used to determine whether any DNA-ziprasidone complex formed, and measuring the amount of any such complex that formed.

The DNA receptors of the array may then be analyzed to identify which of the DNA receptor(s) bind to the ziprasidone and which fail to bind. With this information, which is provided by this EXAMPLE, factors that affect binding may be determined.

EXAMPLE 3

Binding of DNA receptors to DNA probe molecules. A DNA array such as an Affymetrix GeneChip™ may be exposed to a solution of DNA molecules that may or may not be complementary to the DNA on the array. If the DNA in solution is not complementary to any of the DNA on the array, then no binding is expected to occur. If the DNA in solution were complementary to any of the DNA on the array, then some binding would be expected to occur. DNA molecules include the element phosphorus that is detectable using x-ray fluorescence of the phosphorus atoms. After the array is exposed to the solution of DNA, the array may be analyzed using an EDAX Eagle Microprobe x-ray fluorescence microscope. The DNA receptors of the array that bind to the added DNA from the DNA-containing solution may be identified by the phosphorus x-rays, and the amount of added DNA that is associated with each receptor may be quantified by the x-ray fluorescence signal.

Preferably, a baseline x-ray fluorescence signal for each portion of DNA receptor would be obtained before exposing the receptor array to the DNA containing solution to determine the phosphorus content of the DNA receptors of the array. After exposing the array to the DNA solution, the difference in the phosphorus x-ray fluorescence signals after contact and before contact with the DNA solution may be quantified and related to the binding of DNA from the solution to various receptors of the array.

This DNA receptor array used with the EXAMPLE may be replaced with an array that includes other molecules, such as RNA and peptides, to examine the binding of DNA from a solution to these other receptors. RNA may also be used as a probe molecule.

EXAMPLE 4

Binding of drugs to protein receptors. A protein array may be prepared as described in Kukar et al., "Protein Microarrays to Detect Protein-Protein Interactions Using Red and Green Fluorescent Proteins," *Analytical Biochemistry*, vol. 306, pp. 50-54 (2002). This protein array may be exposed to a solution of olanzapine (the active ingredient in Zyprexa®) and aripiprazole (the active ingredient in Abilify™). Olanzapine has the chemical formula $C_{17}H_{20}N_4S$, and aripiprazole has the chemical formula $C_{23}H_{27}Cl_2N_3O_2$. These molecules have the chemical structures shown below.

Olanzapine:

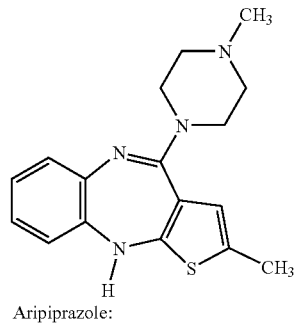

Aripiprazole:

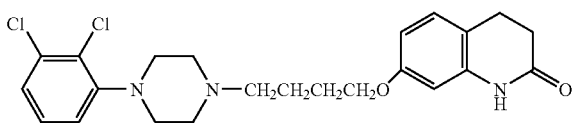

Olanzapine may be detected and quantified by the x-ray fluorescence of its sulfur atom and aripiprazole may be detected and quantified by the x-ray fluorescence of its chlorine atoms.

After the array is exposed to the solution that contains a mixture of aripiprazole and olanzapine, the array may be analyzed using an EDAX Eagle Microprobe x-ray fluorescence microscope. The protein receptors that bind to olanzapine may be identified by the sulfur x-rays. The amount of olanzapine that is associated with each receptor may be quantified by x-ray fluorescence. The protein receptors that bind to aripiprazole may be identified by the chlorine x-rays. The amount of aripiprazole that is associated with each receptor may be quantified by x-ray fluorescence.

Preferably, a baseline x-ray fluorescence signal for chlorine and one for sulfur are measured for each receptor before exposing the receptors to the solution. After contacting the array with the solution, the sulfur and chlorine content of each receptor would be measured again. The difference in the measured sulfur and chlorine x-ray fluorescence signal after contact and before contact with the solution of aripiprazole and olanzapine solution may be quantified and related to the binding of aripiprazole and olanzapine to receptors in the array.

EXAMPLE 5

Binding of drugs to protein receptors. A protein array may be prepared as described in Kukar et al., "Protein Microarrays to Detect Protein—Protein Interactions Using Red and Green Fluorescent Proteins," *Analytical Biochemistry*, vol. 306, pp. 50-54 (2002). This protein array may be exposed to a solution that contains a mixture olanzapine (the active ingredient in Zyprexa®) and acetylsalicylic acid (the active ingredient in aspirin). Olanzapine has the chemical formula $C_{17}H_{20}N_4S$, and acetylsalicylic acid has the chemical formula $C_9H_8O_4$. Olanzapine may be detected and quantified by the x-ray fluorescence of its sulfur atom. Acetylsalicylic acid, however is more difficult to both to detect and differentiate using x-ray fluorescence because it only contains carbon, oxygen and hydrogen, the x-ray fluorescence signals of which are overwhelmed by the corresponding signals in the protein receptors.

After the array is exposed to the solution, the array may be analyzed using an EDAX Eagle Microprobe x-ray fluorescence microscope. The protein receptors that bind to olanzapine in the presence of acetylsalicylic acid may be identified by the net X-ray fluorescence signal from sulfur. The amount of olanzapine that is associated with each receptor may be quantified by x-ray fluorescence.

Preferably, a baseline X-ray fluorescence measurement for the protein receptors of the array would be obtained before exposure to the solution containing acetylsalicylic acid and olanzapine. This analysis may be used to determine the sulfur content of the protein spots on the array. After contacting the array with the solution, the sulfur content of each protein spot may be measured again. The difference in the sulfur after contact and before contact with acetylsalicylic acid and olanzapine solution may be quantified and related to the binding of olanzapine to various protein receptors in the array when acetylsalicylic acid is present.

For comparison, the procedure described above for this EXAMPLE may be repeated using a solution that includes olanzapine without acetylsalicylic acid in order to determine whether the presence of acetylsalicylic acid has any effect on the binding affinity and binding selectivity of olanzapine to the protein receptors. After contacting the array with the solution containing olanzapine (without acetylsalicylic acid), the sulfur content of each protein spot may be measured again. The difference in the sulfur after contact and before contact with olanzapine solution may be quantified and related to the binding of olanzapine to various spots in the array when acetylsalicylic acid is not present. The binding information may be compared to the binding of olanzapine to various spots in the array when acetylsalicylic acid is present.

This EXAMPLE illustrates a particularly important aspect of the present invention, which relates to estimating the therapeutic index of a chemical (in this case, olanzapine) and comparing it to an estimated therapeutic index of a "cocktail" i.e. a mixture of two or more chemicals.

EXAMPLE 6

Personalized Medicine. A question arises relating to which antipsychotic drug, olanzapine or aripiprazole, should be prescribed for a patient. A protein array would be prepared as described, for example, in Kukar et al., "Protein Microarrays to Detect Protein—Protein Interactions Using Red and Green Fluorescent Proteins," *Analytical Biochemistry*, vol. 306, pp. 50-54 (2002).

This protein array would be exposed to a solution of a mixture of olanzapine ($C_{17}H_{20}N_4S$) and aripiprazole ($C_{23}H_{27}Cl_2N_3O_2$). Olanzapine may be detected and quantified by the x-ray fluorescence of its sulfur atom, and aripiprazole may be detected and quantified by the x-ray fluorescence of its chlorine atoms.

After the array is exposed to the solution, the array would be analyzed using an EDAX Eagle Microprobe x-ray fluorescence microscope. The receptor proteins that bind to olanzapine may be identified by their sulfur x-rays. The amount of olanzapine that is associated with each receptor spot may be quantified by x-ray fluorescence. The receptor proteins that bind to aripiprazole may be identified by the chlorine x-rays. The amount of aripiprazole that is associated with each spot may be quantified by x-ray fluorescence.

Preferably, the a baseline x-ray fluorescence signal for each receptor protein of the array is obtained before exposure to the solution. After contacting the array with the solution, the sulfur and chlorine content of each protein receptor spot may be measured again. The difference in the sulfur and chlorine after contact and before contact with the solution may be quantified and related to the binding of aripiprazole and olanzapine to the receptors in the array.

An therapeutic index for this patient for olanzapine and one for aripiprazole may be estimated using the x-ray fluorescence data. These estimated indices may be used to guide the choice of drug to be administered.

EXAMPLE 7

Patient Stratification. A series of protein arrays may be prepared as described in Kukar et al., "Protein Microarrays to Detect Protein—Protein Interactions Using Red and Green Fluorescent Proteins," *Analytical Biochemistry*, vol. 306, pp. 50-54 (2002). The protein arrays would be prepared using samples from participants in clinical trials of pharmaceutical compounds and/or formulations. This is an EXAMPLE for a study for determining the safety and/or efficacy of olanzapine.

The protein arrays described above would be exposed to a solution that includes olanzapine ($Cl_7H_{20}N_4S$). Olanzapine may be detected and quantified by the x-ray fluorescence of its sulfur atom.

After the array is exposed to the solution, the array may be analyzed using an EDAX Eagle Microprobe x-ray fluorescence microscope. The protein receptors that bind to olanzapine may be identified by the x-ray fluorescence signal due to sulfur. The amount of olanzapine that is associated with each protein receptor spot may be quantified by x-ray fluorescence.

Preferably, a baseline x-ray fluorescence signal would be obtained for each receptor before exposure to the solution. This analysis may be used to determine the sulfur content of the protein spots on the array. After contacting the array with the solution, the sulfur content of each protein spot may be measured again. The difference in the sulfur content after contact and before contact with olanzapine solution may be quantified and related to the binding of olanzapine to various protein receptors in the array.

The binding of olanzapine to various proteins or classes of proteins may be then correlated with the results of the clinical trial, in order to correlate protein-olanzapine binding characteristics with safety and/or efficacy of various formulations of olanzapine-based drugs.

It is preferable to use protein arrays rather than DNA arrays for patient stratification, because proteins are believed to control cell functions. However, this method may also be used with DNA arrays, tissue arrays, cellular arrays, and the like.

In summary, the present invention provides a method for measuring binding selectivities between chemicals and receptors. The invention provides significant advantages over known methods for measuring binding selectivity. Known methods often require either radioactive chemicals, or chemicals that include a covalently attached label that fluoresces upon exposure to ultraviolet excitation radiation. Since the invention does not require radioactive or chemically tagged materials, the problems dealing with the handling of radioactive materials and the disposal of radioactively contaminated waste are avoided. Importantly, since the use of artificially tagged materials is not required, there can be no interference from the tag in the evaluation of the binding affinity of the corresponding desired untagged material. Further, in contrast to methods that require tags, the method of the present invention can be used to evaluate the binding affinity of materials that do not fluoresce while exposed to ultraviolet radiation. It should be understood that although tagged materials are not required, they could also be used and this aspect of the invention offers a distinct advantage in that the invention can provide a direct comparison of binding affinity of the untagged chemical with that of the corresponding tagged surrogate. This comparison could validate or invalidate the assumption that a particular untagged chemical and its tagged surrogate have the same binding affinity to a particular substrate.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting a binding event of at least one chemical having at least one heavy element to at least one receptor, comprising:

exposing the at least one bead-supported receptor to X-ray radiation by means of a micro-X-ray fluorescence spectrometer prior to exposing the at least one receptor to the at least one chemical to be tested for binding to the at least one receptor;

measuring the X-ray fluorescence signal intensity of the at least one receptor;

combining the at least one bead-supported receptor and the at least one chemical then allowing a receptor-chemical complex to form; wherein the at least one chemical comprises at least one heavy element selected from the group consisting of P, Cl, F, S, and Br;

removing any at least one chemical that is not part of the receptor-chemical complex;

exposing the receptor-chemical complex to X-ray radiation from an X-ray excitation source;

measuring the X-ray fluorescence signal intensity of the at least one heavy element in the receptor-chemical complex; and evaluating the receptor-chemical complex X-ray fluorescence signal intensity such that when the heavy element is present in both the at least one chemical and the at least one receptor, an assessed difference in the X-ray signal intensities of the receptor-chemical complex and the at least one receptor signifies that a binding event has occurred between the at least one chemical and the at least one receptor; and when the heavy element is only present in the at least one chemical but not the at least one receptor, the X-ray signal intensity of the receptor-chemical complex signifies that a binding event has occurred between the at least one chemical and the at least one receptor.

2. The method of claim 1 wherein the at least one chemical comprises more than one chemical.

3. The method of claim 1 wherein the at least one heavy element comprises more than one heavy element selected from the group consisting of P, Cl, F, S, and Br.

4. The method of claim 1 wherein the at least one chemical comprises more than one chemical, wherein the at least one bead-supported receptor comprises more than one bead-supported receptor and wherein the at least one heavy element comprises more than one heavy element selected from the group consisting of P, Cl, F, S, and Br.

5. The method of claim 4 wherein each at least one chemical binds to at least one receptor with different affinities.

\* \* \* \* \*